United States Patent
Ortega et al.

(10) Patent No.: US 11,980,762 B2
(45) Date of Patent: May 14, 2024

(54) SYSTEM FOR BRUGADA SYNDROME DETECTION AND TREATMENT VIA ELECTRICAL STIMULATION

(71) Applicant: NewStim, Inc., La Lucila (AR)

(72) Inventors: Daniel Felipe Ortega, San Fernando (AR); Luis Dante Barja, Escobar (AR)

(73) Assignee: NEWSTIM, INC., La Lucila (AR)

( * ) Notice: Subject to any disclaimer, the term of this patent is extended or adjusted under 35 U.S.C. 154(b) by 0 days.

(21) Appl. No.: 17/872,871

(22) Filed: Jul. 25, 2022

(65) Prior Publication Data
US 2022/0355116 A1    Nov. 10, 2022

Related U.S. Application Data

(63) Continuation of application No. 16/700,831, filed on Dec. 2, 2019, now Pat. No. 11,395,922, which is a
(Continued)

(51) Int. Cl.
*A61N 1/365*    (2006.01)
*A61B 5/00*    (2006.01)
(Continued)

(52) U.S. Cl.
CPC ............ *A61N 1/36507* (2013.01); *A61B 5/35* (2021.01); *A61B 5/363* (2021.01); *A61B 5/366* (2021.01);
(Continued)

(58) Field of Classification Search
CPC ......... A61B 5/327; A61B 5/364; A61B 5/366; A61B 5/361; A61B 5/363; A61B 5/35;
(Continued)

(56) References Cited

U.S. PATENT DOCUMENTS

| 7,512,440 B2 | 3/2009 | Ortega et al. |
| 8,005,544 B2 | 8/2011 | Zhu et al. |

(Continued)

OTHER PUBLICATIONS

Kathy L. Lee et al., "Prevention of Ventricular Fibrillation by Pacing in a Man with Brugada Syndrome", J Cardiovasc Electrophysiol., vol. 11, pp. 935-937, (Aug. 2000).
(Continued)

*Primary Examiner* — Jon Eric C Morales
(74) *Attorney, Agent, or Firm* — Leonid Kisselev

(57) ABSTRACT

Brugada syndrome and related forms of ion channelopathies, including ventricular asynchrony of contraction, originate in the region near the His bundle or para-Hisian regions of the heart. Manifestations of Brugada syndrome can be corrected by delivering endocardial electrical stimulation coincident to the activation wave front propagated from the atrioventricular (AV) node early enough to compensate for the conduction problems that start in those regions. The stimulation can include waveforms of the same polarity delivered to a site within the region near the His bundle or para-Hisian regions of the heart associated with a low cardiac electrical asynchrony level or can include at least two single-phased superimposed waveforms of opposite polarity delivered through a pair of pacing electrodes relative to a reference electrode, which can be delivered to any site within the region near the His bundle or para-Hisian regions. Defibrillation can also be used to terminate an arrhythmia.

1 Claim, 27 Drawing Sheets

Related U.S. Application Data continuation of application No. 15/934,811, filed on Mar. 23, 2018, now Pat. No. 10,493,284, which is a continuation-in-part of application No. 15/474,950, filed on Mar. 30, 2017, now Pat. No. 10,335,600.

(51) Int. Cl.

| | | |
|---|---|---|
| *A61B 5/35* | (2021.01) | |
| *A61B 5/363* | (2021.01) | |
| *A61B 5/366* | (2021.01) | |
| *A61N 1/05* | (2006.01) | |
| *A61N 1/362* | (2006.01) | |
| *A61N 1/368* | (2006.01) | |
| *A61N 1/37* | (2006.01) | |
| *A61N 1/39* | (2006.01) | |

(52) U.S. Cl.
CPC .......... *A61B 5/4836* (2013.01); *A61N 1/0563* (2013.01); *A61N 1/0565* (2013.01); *A61N 1/059* (2013.01); *A61N 1/3622* (2013.01); *A61N 1/3682* (2013.01); *A61N 1/3706* (2013.01); *A61N 1/3956* (2013.01); *A61N 1/39622* (2017.08); *A61N 1/3987* (2013.01); *A61N 1/3627* (2013.01); *A61N 1/3684* (2013.01)

(58) Field of Classification Search
CPC ......... A61B 5/349; A61B 5/347; A61B 5/346; A61B 5/335; A61B 5/333; A61N 1/3627; A61N 1/3621; A61N 1/362; A61N 1/365; A61N 1/36592
See application file for complete search history.

(56) References Cited

U.S. PATENT DOCUMENTS

| | | |
|---|---|---|
| 8,010,191 B2 | 8/2011 | Zhu et al. |
| 8,010,192 B2 | 8/2011 | Zhu et al. |
| 8,014,861 B2 | 9/2011 | Zhu et al. |
| 8,050,756 B2 | 11/2011 | Zhu et al. |
| 8,285,376 B2 | 10/2012 | Ortega et al. |
| 8,290,586 B2 | 10/2012 | Zhu et al. |
| 8,326,423 B2 | 12/2012 | Zhu et al. |
| 8,346,358 B2 | 1/2013 | Ortega et al. |
| 8,423,139 B2 | 4/2013 | Zhu et al. |
| 8,428,715 B2 | 4/2013 | Ortega et al. |
| 8,437,848 B2 | 5/2013 | Ortega et al. |
| 9,392,949 B2 | 7/2016 | Ortega et al. |
| 11,395,922 B2 * | 7/2022 | Ortega .................. A61N 1/059 |
| 2003/0083586 A1 | 5/2003 | Ferek-Petric |
| 2004/0267142 A1 | 12/2004 | Paul |
| 2006/0136001 A1 | 6/2006 | Ortega et al. |
| 2008/0319496 A1 | 12/2008 | Zhu et al. |
| 2008/0319499 A1 | 12/2008 | Zhu et al. |
| 2008/0319500 A1 | 12/2008 | Zhu et al. |
| 2008/0319501 A1 | 12/2008 | Zhu et al. |
| 2009/0005830 A1 | 1/2009 | Zhu et al. |
| 2009/0005832 A1 | 1/2009 | Zhu et al. |
| 2009/0005846 A1 | 1/2009 | Zhu et al. |
| 2009/0054942 A1 | 2/2009 | Zhu et al. |
| 2009/0137916 A1 | 5/2009 | Maison-Blanche et al. |
| 2009/0187226 A1 | 7/2009 | Ortega et al. |
| 2010/0198291 A1 | 8/2010 | Sambelashvili et al. |
| 2011/0307026 A1 | 12/2011 | Zhu et al. |
| 2011/0319956 A1 | 12/2011 | Zhu et al. |
| 2012/0041500 A1 | 2/2012 | Zhu et al. |
| 2012/0041503 A1 | 2/2012 | Zhu et al. |
| 2012/0053651 A1 | 3/2012 | Zhu et al. |
| 2012/0101539 A1 | 4/2012 | Zhu et al. |
| 2013/0041423 A1 | 2/2013 | Zhu et al. |
| 2013/0096638 A1 | 4/2013 | Ortega et al. |
| 2014/0371613 A1 | 12/2014 | Narayan et al. |
| 2018/0280695 A1 | 10/2018 | Ortega |

OTHER PUBLICATIONS

Hiroshi Nakagawa et al., "Para-Hisian pacing: Useful clinical technique to differentiate retrograde conduction between accessory atrioventricular pathways and atrioverticular nodal pathways", Heart Rhythm, vol. 2, No. 6, pp. 667-672, (Jun. 2005).

Deshmukh et al., "Permanent, Direct His-Bundle Pacing: A novel Approach to Cardiac Pacing in Patients With Normal His-Purkinje Activation", Circulation, vol. 101, pp. 867-877, (2000).

Sami Viskin, M.D., Inducible Ventricular Fibrillation in the Brugada Syndrome: Diagnostic and Prognostic Implications:, J Cardiovasc Electrophysiol., vol. 14, No. 5, pp. 458-460, (May 2003).

Braunwald, "Heart Disease—A Textbook of Cardiovascular Medicine," p. 904 (8th ed. 2008).

* cited by examiner

60

80

Fig. 5 (con'd).
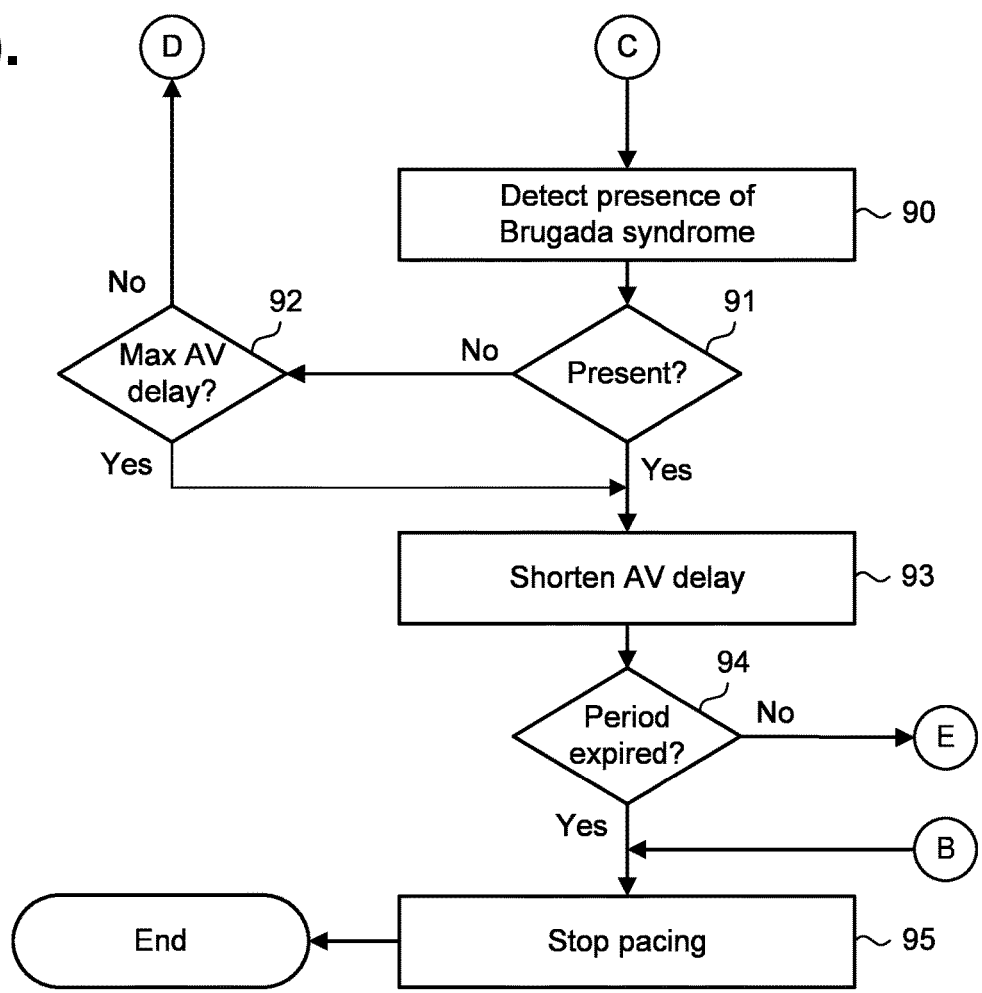

100

130

SYSTEM FOR BRUGADA SYNDROME DETECTION AND TREATMENT VIA ELECTRICAL STIMULATION

CROSS-REFERENCE TO RELATED APPLICATION

This non-provisional patent application is a continuation of U.S. Pat. No. 11,395,922, issued Jul. 26, 2022, which is a continuation of U.S. Pat. No. 10,493,284, issued Dec. 3, 2019, which is a continuation-in-part of U.S. Pat. No. 10,335,600, issued Jul. 2, 2019, the disclosures of which are incorporated by reference.

FIELD

This application relates in general to treatment of cardiac rhythm disorders and, in particular, to a system for Brugada syndrome detection and treatment via electrical stimulation.

BACKGROUND

Brugada syndrome is a distinct form of genetically-determined idiopathic cardiac arrhythmia syndrome that can lead to syncope, cardiac arrest and sudden cardiac death (SCD). The syndrome is a genetic form of cardiac rhythm disorder caused by an inherited ion channelopathy. Brugada syndrome has been observed in the electrocardiograms of otherwise healthy young individuals without evidence of structural heart disease who are of Southeast Asian descent. Men are eight to ten times more likely to suffer Brugada syndrome. The syndrome has an autosomal-dominant pattern of transmission in about half of the familial cases observed and primarily affects Southeast Asian men, especially Thai and Laotian, in the 30-50 year age range, with a median age of 41 years.

The prognosis in Brugada syndrome is poor. Although the exact incidence of SCD due to Brugada syndrome is unknown, the magnitude of the problem has been estimated to range from 180,000 to 450,000 deaths annually in the United States alone. Further, about 2.5% of all cardiac arrest cases in which the patient showed no clinically identifiable cardiac abnormalities have been attributed to Brugada syndrome. The syndrome also accounts for 4% to 12% of all SCDs in genetically pre-disposed individuals, and a 40% mortality rate has been observed in symptomatic patients at two to three years follow up, with a 2% to 4% mortality rate in asymptomatic patients. During electrophysiologic studies (EPS), asymptomatic patients with induced ventricular tachycardia (VT) or ventricular fibrillation (VF) exhibited four times more SCD than non-inducible patients.

The cause of death in Brugada syndrome is due to VF, yet the precise mechanism underlying the electrocardiographic changes observed in symptomatic patients having Brugada syndrome is unknown. Pathologically, in 20% of observed cases, the syndrome has been associated with mutations in SCN5A gene expression, located in chromosome 3, which encodes for sodium ion channel transport to cell membranes of cardiac myocytes. Loss-of-function mutations in this gene have been theorized to lead to a failure of the action potential dome to develop, that in turn causes persistent ST segment elevation. The clinical events observed coincident to the electrocardiographic markers of Brugada syndrome, from syncope to VT to VF to SCD, are triggered by polymorphic ventricular arrhythmias, whose mechanism could be a Phase 2 reentry in the area around the right ventricular outflow tract.

Conventional approaches to treating Brugada syndrome focus on preventing or ameliorating VT and VF. For instance, implantable cardiac rhythm management devices, particularly automatic implantable cardioverter-defibrillator (ICDs), and, to a lesser extent, transiently-introduced electrophysiology catheters, apply a therapy based on the reversion of already-established polymorphic arrhythmias, such as described in Lee et al., "Prevention of Ventricular Fibrillation by Pacing in a Man with Brugada Syndrome," J. Cardiovasc. Electrophysiol., Vol. 11, pp. 935-937 (August 2000), the disclosure of which is incorporated by reference. Similarly, Quinidine-based pharmaceutical therapies have also been used to effectively prevent VF induction and suppress spontaneous arrhythmias. Finally, surgical interventions through ablation at the right ventricular outflow tract level have been explored. Notwithstanding, these approaches constitute aggressive interventions and are impracticable to use on the large population that is theorized to have the Brugada syndrome, as only a small percentage will develop VT or VF, or experience cardiac arrest or SCD.

Therefore, a need remains for an approach to proactively treating the conduction and activation problems underlying the Brugada syndrome, rather than focusing on only avoiding or alleviating the deleterious sequelae of the syndrome.

A further need exists for an approach that can utilize commercially available cardiac arrhythmia devices for treating the conduction and activation problems underlying the Brugada syndrome.

SUMMARY

Brugada syndrome and related forms of ion channelopathies, including ventricular asynchrony of contraction, originate around the right ventricular outflow tract, the region near the His bundle or para-Hisian region of the heart. Manifestations of Brugada syndrome can be corrected by delivering endocardial electrical stimulation coincident to the activation wave front propagated from the atrioventricular (AV) node. The stimulation can include waveforms of the same polarity or can include at least two single-phased superimposed waveforms of opposite polarity delivered through a pair of pacing electrodes relative to a reference electrode. Whereas delivering stimulation that includes at least two single-phased superimposed waveforms of opposite polarity is effective at correcting manifestations of the Brugada syndrome when delivered to any site within the region near the His bundle or para-Hisian region, the Brugada syndrome manifestations can also be corrected when stimulation that only includes waveforms of the same polarity is delivered to a site within the region near the His bundle or para-Hisian region that is selected because of a low level of cardiac electrical asynchrony associated with delivering pacing to that site. The approach involving only waveforms of the same polarity may be implemented using commercially available pacing electrodes, and thus may be used to treat the Brugada syndrome even when all of the components necessary to deliver the at least two single-phased superimposed waveforms of opposite polarity are not readily available.

In one embodiment, a system for Brugada syndrome detection and treatment via electrical stimulation is provided. The system includes a cardiac pacing device including a pulse generator and at least one pacing electrode that is electrically coupled to the pulse generator via an endocardial lead, the at least one pacing electrode configured to be positioned in one of a plurality of potential pacing sites that is selected based on a level of cardiac electrical asynchrony associated with that potential pacing site and based on a defibrillation shock being capable of being delivered to the site, the selected potential pacing site located in one of a region near the His bundle and a para-Hisian region of a patient's heart, the pulse generator configured to deliver through the at least one pacing electrode therapeutic electrical stimulation substantially coincidentally to propagation of an activation wave front proceeding from the atrioventricular node of the patient's heart when the at least one pacing electrode is positioned at the selected potential pacing site, the cardiac pacing device further including a cardioverter defibrillator coupled to the endocardial lead; and a diagnostic module operatively coupled to the pulse generator and configured to sense via at least one sensing electrode physiology indicative of a presence of Brugada syndrome in the patient, to detect the presence of the Brugada syndrome, the diagnostic module further configured to control the pulse generator in delivering the electrical therapeutic electrical stimulation at the selected potential pacing site in response to the presence of Brugada syndrome, and to control the cardioverter defibrillator to deliver via the endocardial lead the defibrillator shock to the patient.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Implantable cardiac rhythm management (CRM) devices include pacemakers, implantable cardioverter-defibrillators (ICDs), and cardiac resynchronization therapy (CRT) devices. CRM devices and, to a lesser extent, transiently-introduced electrophysiology catheters, such as used to induce ventricular arrhythmias during electrophysiologic studies (EPS), currently provide the only effective means for treating the sequelae VT and VF triggered by the syndrome and thereby help to prevent SCD. However, these devices focus on preventing or ameliorating VT and VF, rather than directly addressing the elimination of the electrocardiographic pattern typical of Brugada syndrome and related forms of channelopathies and cardiac asynchrony disorders.

Conventional arrhythmia management using CRM devices is episode-focused. Changes in heart rhythm are monitored by a CRM device as arrhythmic episodes potentially requiring therapy to convert, mitigate, or interrupt the dysrhythmia. Pacemakers, for instance, manage bradycardia, which is an abnormally slow or irregular heartbeat, by delivering pacing stimuli to restore normal sinus rhythm through electrodes provided on endocardial pacing leads. Implantable cardioverter defibrillators (ICDs) treat tachycardia, which are abnormally fast and life threatening heart rhythms, through high energy cardioversion, defibrillation shocks, or anti-tachycardia pacing.

Figure 1:
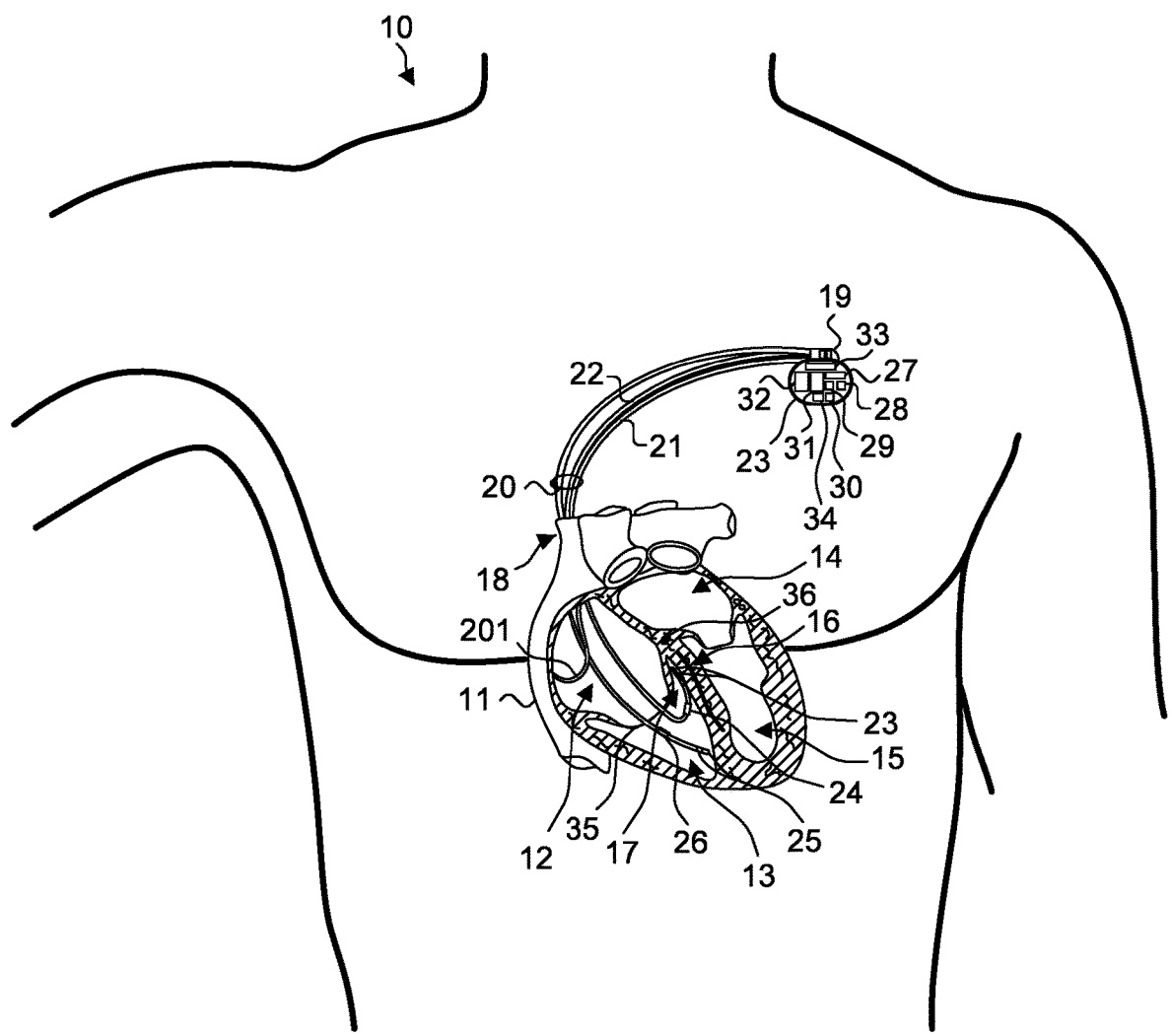
FIG. 1 is a front anatomical diagram showing placement of an implantable cardiac rhythm management device in a male patient for treating Brugada syndrome, in accordance with one embodiment.

Brugada syndrome, as well as other forms of conduction problems that start in the His and para-Hisian regions, such as ventricular asynchrony of contraction, can be corrected by actively stimulating those regions of the heart as the activation wave front coming from the atrioventricular (AV) node enters using an implantable CRM device. FIG. 1 is a front anatomical diagram showing placement of an implantable CRM device 19 in a male patient 10 for treating Brugada syndrome, in accordance with one embodiment. Depending upon type, CRM devices can provide therapeutic electrical stimuli for up to three chambers of the heart. Single-chamber CRM devices rely on one endocardial lead attached to either the right atrium or right ventricle, while dual-chamber CRM devices utilize a pair of endocardial leads attached to the right atrium and right ventricle. Triple-chamber CRM devices use endocardial leads in the right atrium and right ventricle and coronary venous leads in the left ventricle.

The implantable CRM device 19 is preferably at least a dual-chamber CRM device that is surgically implanted subcutaneously in the patient's pectoral region or other suitable location in situ. A pair of dual-chamber endocardial leads 21, 22 are guided through the left subclavian vein (not shown) and superior vena cava 18 into the right atrium 12 and right ventricle 13 of the heart 11 for providing cardiac physiological monitoring within and for delivering electrical therapy to the patient's heart 11. The implantable CRM device can further include an additional endocardial lead 201 that is similarly guided into the heart into the right atrium 12 for sensing atrial activity. For the sake of clarity, the endocardial leads 201, 21, 22 are shown leading directly into the heart 11, although different placement and orientation may be used during actual implantation. Other forms of CRM may require placement of endocardial leads in the left atrium 14 or left ventricle 15 of the heart 11. For the sake of completeness, two endocardial leads 21, 22 are shown, although only the endocardial lead 21 and its pacing electrodes 23 that are distally located in the region near the His bundle 16 or para-Hisian region 17 are directly addressed in the delivery of pacing therapy for treating Brugada syndrome, as can be seen with reference to FIG. 19, which is a front anatomical diagram showing placement of an implantable CRM device 19 in a male patient 10 for treating Brugada syndrome, in accordance with a further embodiment.

Figure 19:
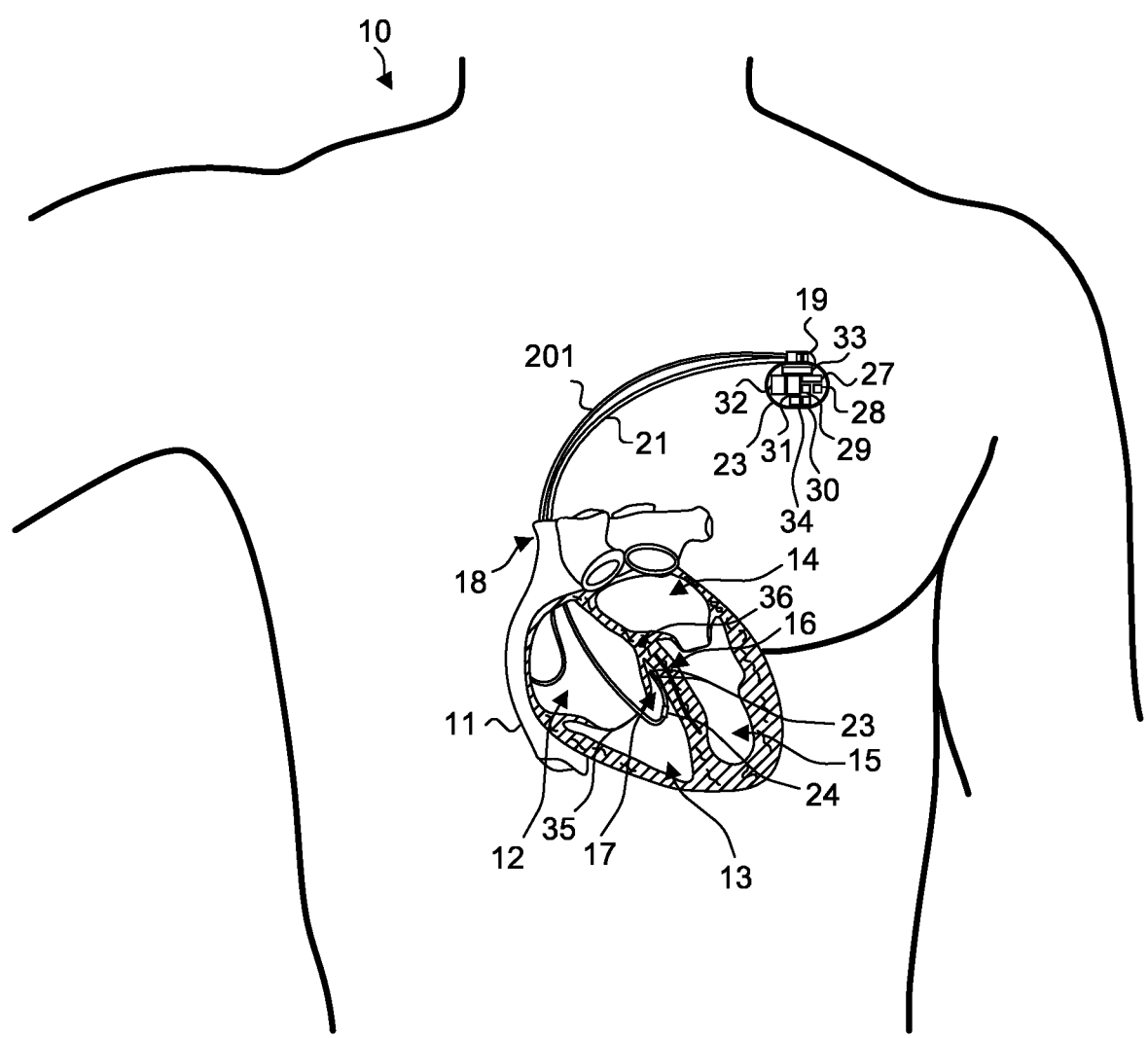
FIG. 19 is a front anatomical diagram showing placement of an implantable CRM device in a male patient for treating Brugada syndrome, in accordance with a further embodiment.
Figure 20:
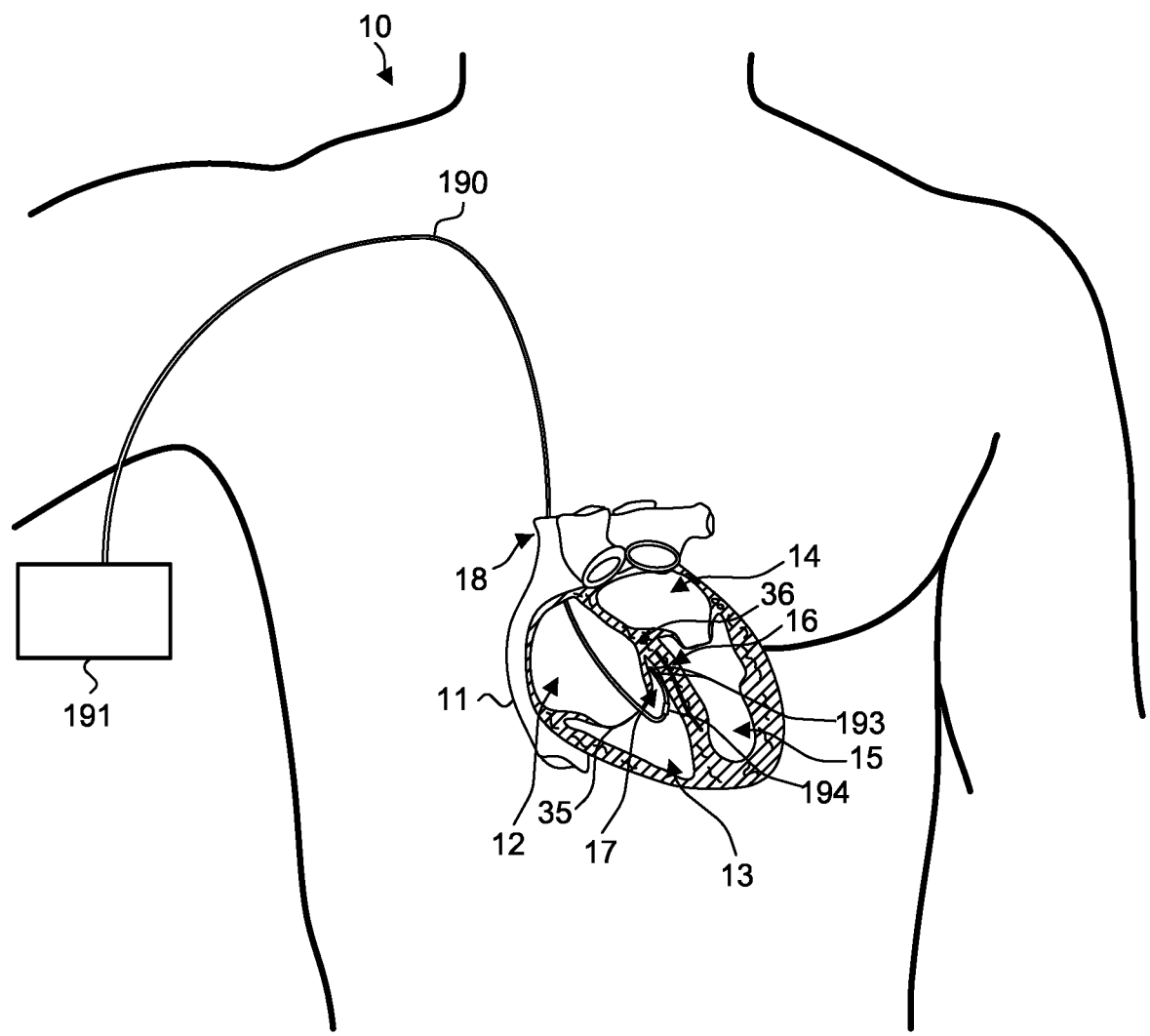
FIG. 20 is a front anatomical diagram showing placement of a transiently-introduced catheter in a male patient for treating Brugada syndrome, in accordance with one embodiment.
Figure 21:
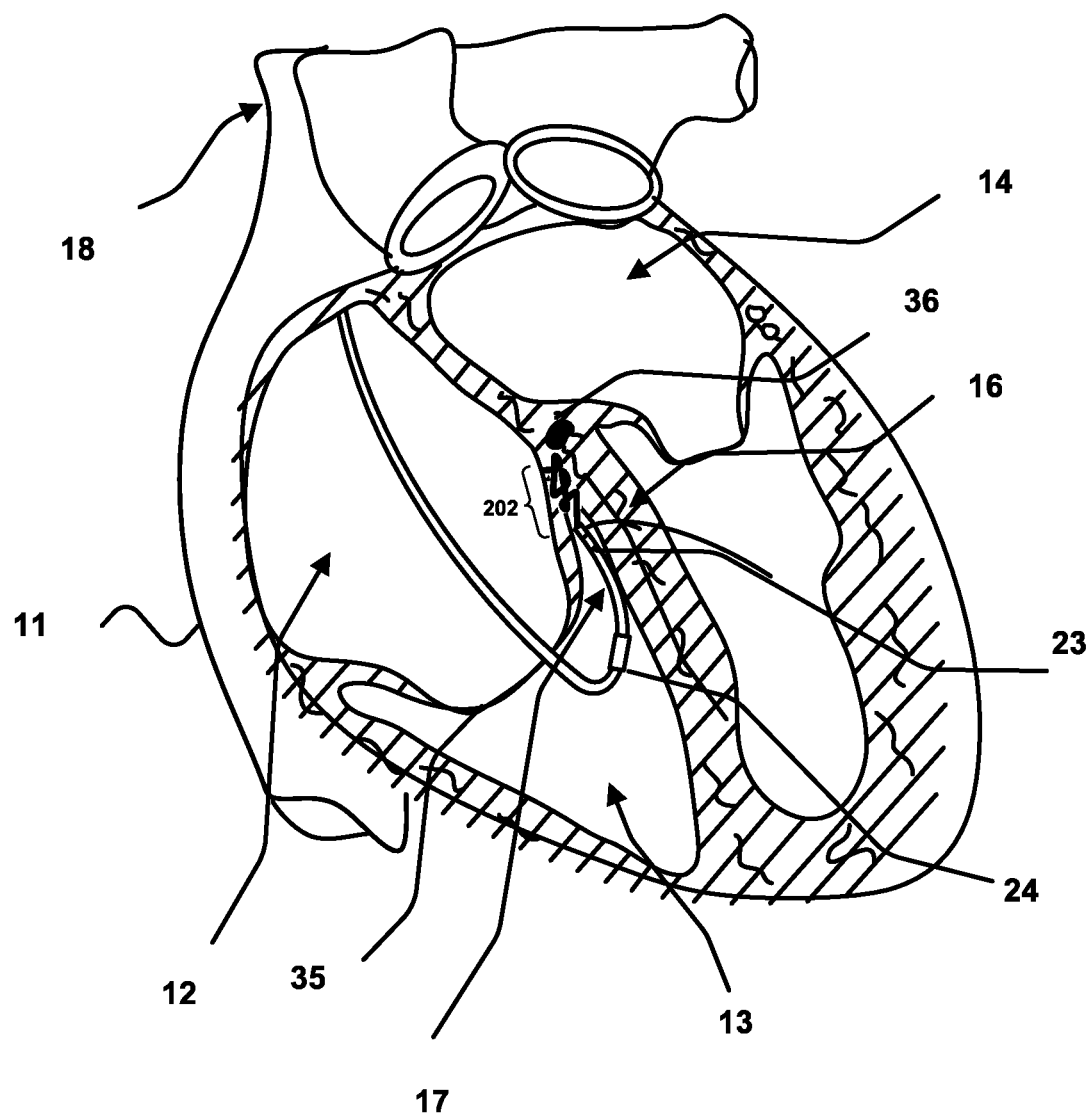
FIG. 21 is a close-up view of FIG. 19 showing the endocardial lead within the heart in accordance with one embodiment.

The endocardial leads 21, 22, 201 are screw-in leads FIG. 21 is a close-up view of FIG. 19 showing the endocardial lead 21 within the heart 11 in accordance with one embodiment. As can be seen with reference to FIG. 21, the screw 202 portion of the lead 21 secures the lead within the cardiac tissue being stimulated. While the screws 202 are not shown with reference to FIGS. 1 and 19, the screws 202 are also parts of the endocardial leads 21 shown with reference to these FIGUREs. Likewise, the screw 202 is a part of a catheter 190 shown with reference to FIG. 20.

In the general sense, electrical stimuli can be delivered through pacing electrodes 23, 25 respectively on the distal ends of each of the endocardial leads 21, 22, although only the pacing electrodes 23 that are distally located in the region near the His bundle 16 or the para-Hisian region 17 are of interest herein. By way of example, the pacing electrodes 23, 25 are bipolar electrodes, but the pacing electrodes could also be unipolar or tripolar. In a further embodiment, the endocardial leads 21, 22 can also respectively include sensing electrodes 24, 26 located near their distal ends for monitoring physiology indicative of a presence of Brugada syndrome. In a still further embodiment, the pacing electrodes 23, 25 could be alternatively re-purposed to sense physiology between deliveries of electrical stimuli.

The implantable CRM device 19 also encloses operational circuitry within a hermetically-sealed housing 28, which generally includes control circuitry 27; inductive transducer 28; oscillator 29; wireless transceiver 30; memory 31; and power source 32, which provides a finite power supply for the operational circuitry. The control circuitry 27 implements the implantable CRM device's functionality and controls pulse generator output circuitry 33 for delivering electrical stimulation therapy through the pacing electrodes 23, 25 to the heart 11, and sensing amplifiers 34 for monitoring cardiac physiology in the heart 11 through the sensing electrodes 24, 26. The transducer 28 provides inductive signal conversion to enable remote parametric programming of the implantable CRM device 19 and stored physiologic data offload from the memory 31 through an external programmer or similar inductively-coupled device, as further described infra with reference to FIG. 11. The oscillator 29 regulates internal CRM device operation by controlling timing. The wireless transceiver 30 enables wireless communications with an external computer or similar wirelessly-interfaced device, as also further described infra with reference to FIG. 11. Finally, the memory 31 stores monitored cardiac physiology, such as the patient's monitored physiometry; environmental data, for instance, ambient temperature or time of day; and parametric information, including programming, status, and device operational characteristics for the implantable CRM device 19 proper. The parametric information can include pacing parameters, including electrical stimuli waveform, voltage, amplitude, phase, pulse width, rate, inter-pulse delay, pacing duration, inter-pacing delay, and so forth. Still other kinds of parametric information and pacing parameters are possible.

Figure 2:
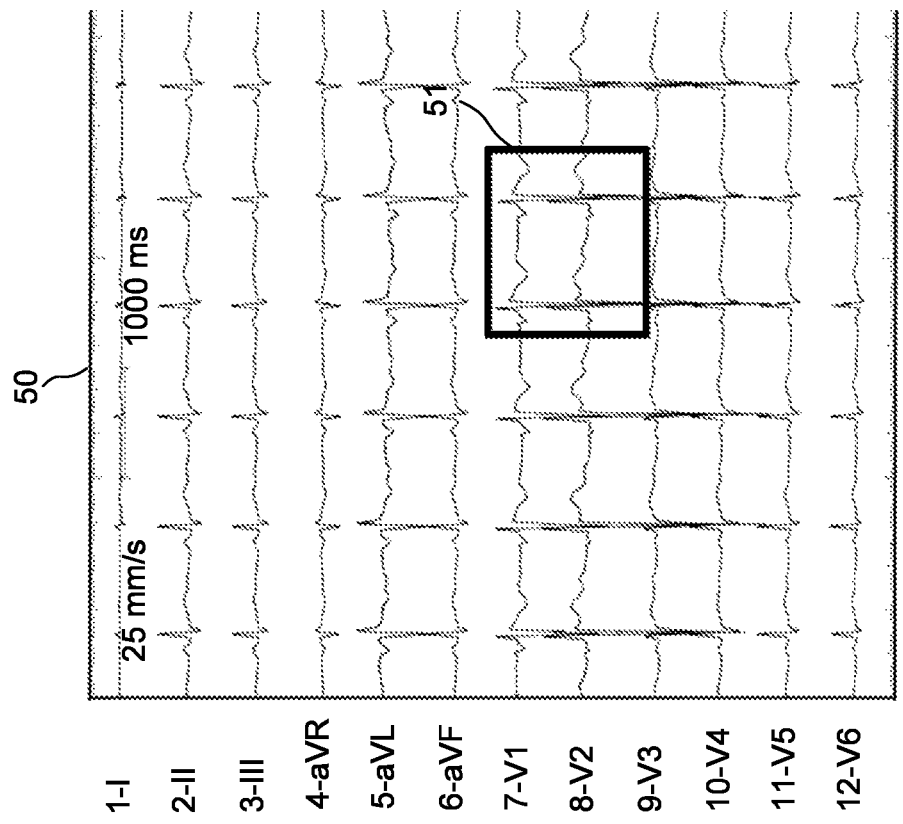
FIGS. 2 and 3 are graphs showing, by way of example, 12-lead electrocardiograms for patients exhibiting Brugada syndrome.
Figure 3:
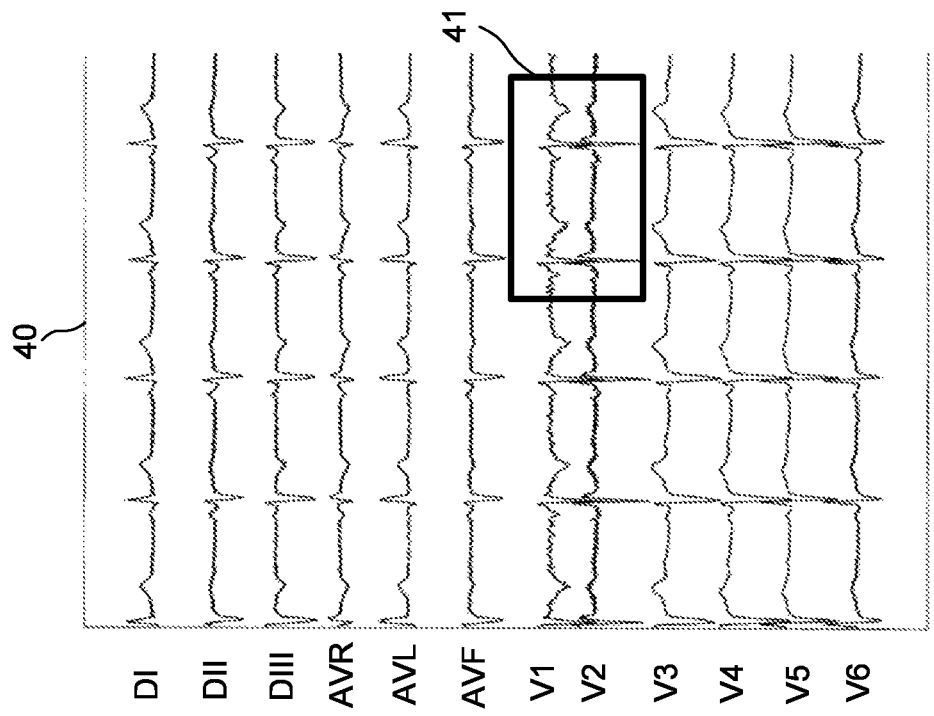

Brugada syndrome is a genetic disease characterized by abnormal electrocardiogram findings and an increased risk of cardiac arrest and SCD, such as described in Braunwald, "Heart Disease—A Textbook of Cardiovascular Medicine," p. 904 ($8^{th}$ ed. 2008), the disclosure of which is incorporated by reference. FIGS. 2 and 3 are graphs respectively showing, by way of example, 12-lead electrocardiograms 40, 50 for patients exhibiting Brugada syndrome. The syndrome is primarily characterized by an electrocardiogram 40, 50, or similar temporally-captured cardiac cycle physiology, that exhibits an ST segment elevation in the anterior precordial (V1, V2, V3) leads with QRS complexes exhibiting an image of right bundle branch block in the right precordial leads and an elevation at the J point, which are respectively indicated by boxes 41, 51. In general, the electrocardiogram pattern can be of three types, Type 1 with coved-type ST segment, Type 2 with saddleback ST segment and Type 3 with ST segment elevated less than 1 mm.

Clinically, a QRS duration in lead V2 longer than 90 msec combined with an inferolateral J wave or horizontal ST segment morphology following the J wave can serve as predictors of cardiac events for purposes of treating Brugada syndrome. Referring back to FIG. 1, Brugada syndrome, as well as other forms of related conduction problems, can be corrected by actively stimulating the region near the His bundle 16 or the para-Hisian region 17. Two forms of pacing are used. In the first form, electrical stimulation is triggered by the direct early detection of the arrival of an activation wave front from the AV node 36 to the His bundle 16 or para-Hisian regions 17 of the patient's heart 11, as further described infra with reference to FIG. 4. In the second form, electrical stimulation is triggered by an atrial activity, which can be sensed in lieu of or in addition to His or para-Hisian events, as further described infra with reference to FIG. 5.

Empirically, the electrocardiographic pattern characteristic of Brugada syndrome can be eliminated by using an ample combination of pacing sites and electrical stimulation amplitudes around the region near the His bundle 16 or in the para-Hisian region 17, on either the right atrial and right ventricular sides of the tricuspid valve 35, or in some combination thereof. A virtual pacing electrode, when applied to the right region of the septum, allows the Brugada syndrome electrocardiographic pattern to be normalized and the conduction and activation abnormalities that created the pattern to be corrected. In one embodiment, the endocardial lead 21 is guided through the tricuspid valve 35 and the pacing electrodes 23 are placed in the para-Hisian region 17 towards the right ventricular outflow tract, such as described in Nakagawa et al., "Para-Hisian pacing: Useful clinical technique to differentiate retrograde conduction between accessory atrioventricular pathways and atrioventricular nodal pathways," Heart Rhythm, Vol. 2(6), pp. 667-72 (June 2005), the disclosure of which is incorporated by reference. In a further embodiment, the pacing electrodes 23 are placed in the region near the His bundle 16 at a point near the AV septum, superior to the tricuspid valve 35, such as described in Deshmukh et al., "Permanent, Direct His-Bundle Pacing," Circulation, Vol. 101, pp. 869-977 (2000), the disclosure of which is incorporated by reference. As further described below, there are multiple sites within both the para-Hisian region 17 and the region near the His bundle 16 where the pacing electrodes 23, 25 can be positioned, and, in one embodiment, the optimum site for delivery of the pacing can be selected by evaluating cardiac asynchrony associated with delivering pacing to that site.

Empirically, these pacing locations have been found to deliver optimum stimulation therapy when using an implanted endocardial pacing lead 21 or, in a further embodiment, when using an transiently-introduced electrophysiology catheter, shown below with reference to FIG. 20. In one embodiment, the pulse generator 33 delivers a ventricular pacing output of at least two single-phase superimposed waveforms of opposite polarity with respect to an indifferent (reference) electrode (not shown). The indifferent electrode could be located as a third electrode in a tripolar lead, an exposed metallic surface on the implantable CRM device's housing 28, an electrode connected to the implantable CRM device 19 proper, or other type of reference voltage lead. A pulse generator and single-phase superimposed waveforms of opposite polarity as used to bypass a conduction defect causing an asynchronous contraction of the heart, such as described in U.S. Patent App. Pub. No. 2012/0053651, the disclosure of which is incorporated by reference, could be used as the implantable CRM device 19.

The delivery of the two single-phased superimposed waveforms of opposite polarity with respect to the indifferent electrode may require a redesign of existing hardware platforms in commercially available implantable devices. As such redesigns may require investment of additional resources, the delivery of the two-single phased superimposed waveforms through the electrodes 23, 25 may not always be practicable.

Accordingly, in a further embodiment, the CRM device 19 can achieve normalization of the Brugada syndrome electrocardiographic pattern and the correction of the conduction and activation abnormalities through delivery of only conventional pacing waveforms: pulse waveforms of the same polarity with respect to the indifferent electrode to a site within the region near the His bundle 16 or the para-Hisian region 17. As further described below, the site selection for the stimulation is associated with a low level of cardiac electrical asynchrony. The electrical therapeutic stimulation can be delivered through a single pacing electrode 23, 25 coupled to the lead 21, though in a further embodiment, multiple pacing electrodes 23, 25 can be used to deliver the stimulation. While, as described above, the CRM device 19 can include a pacemaker, an ICD, and cardiac resynchronization therapy (CRT) devices, including an ICD into the CRM device 19 provides additional protection for the patient against SCD. Accordingly, if the CRM device 19 includes an ICD, the endocardial lead 21 coupled to the pacing electrode 23, 25 can be a defibrillation lead, though other kinds of leads 21 are possible. The delivery of the therapeutic electrical stimulation of pulses of the same polarity can be performed using commercially available electrodes, making the CRM device 19 more widely available for treatment of the Brugada syndrome.

As further described below, the normalization of the Brugada syndrome electrocardiographic pattern can also be achieved using a transiently-introduced electrophysiology catheter, in conjunction with an external pulse generator, such as used to induce ventricular arrhythmias during EPS. FIG. 20 is a front anatomical diagram showing placement of a transiently-introduced catheter 19 in a male patient for treating Brugada syndrome, in accordance with one embodiment. The catheter 190 is connected to the external pulse generator 191 and can deliver stimulation to the para-Hisian 17 region or the His bundle 16 via at least one pacing electrode 193 (which can be a bipolar electrode, though in a further embodiment, the electrode can be a tripolar or a unipolar electrode). The catheter 190 can further include at least one sensing electrode 194 located near the catheter's distal end for monitoring physiology indicative of a presence of Brugada syndrome, which can be processed by processing circuitry (not shown) coupled to the external pulse generator 191. In a further embodiment, a further catheter (not shown) can be introduced into the right atrium 12 for sensing atrial activity, with the sensed activity being processed by the processing circuitry coupled to the external pulse generator 191. The catheter 190 can deliver conventional pacing or pacing that involves delivery of at least two single-phase superimposed waveforms of opposite polarity with respect to an indifferent (reference) electrode.

Multiple potential sites where the pacing electrode 23, 25, 193 within the region near the His bundle 16 or the para-Hisian region can be positioned are possible. While electrical therapeutic stimulation that employs at least two single-phased superimposed waveforms of opposite polarity with respect to the indifferent electrode is effective when applied to any of the potential pacing sites within the region near the His bundle 16 or the para-Hisian region 17, treatment of the Brugada syndrome using pulse waveforms of the same polarity requires careful selection of the pacing site due to potential cardiac asynchrony. Cardiac pacing can contribute to appearance of intraventricular and interventricular electrical asynchrony in a patient, which in turn can interfere with effects of anti-Brugada pacing.

Applying pacing utilizing pulse waveforms of the same polarity to a pacing site that is associated with a low level of intraventricular electrical asynchrony has been empirically shown to normalize the Brugada syndrome pattern and correct the conduction and activation abnormalities caused by the syndrome. As further described below with reference to FIGS. 5 and 6 the selection of the pacing site can be accomplished using an apparatus that quantifies the levels of asynchrony present when pacing through the electrode 23, 25, 193 is applied to a plurality of potential pacing sites and the pacing site that is associated with the lowest level of cardiac asynchrony is selected as the position of the electrode 23, 25, 193. Such apparatus can be the one described in the U.S. Pat. No. 9,392,949, issued on Jul. 19, 2016, to Ortega et al, the disclosure of which is incorporated by reference. Briefly, the apparatus obtains, using either surface electrocardiography or intracardiac electrodes, cardiac signals from two locations of the patient's heart; extracts signal information; segments QRS complexes of the first signal and the second signal based on the extracted information; cross-correlates the QRS complexes of the first and second signal to produce a correlation signal; and calculates an index indicative of the level of asynchrony. Other apparatuses for establishing the level of asynchrony are possible. The asynchrony measured can be interventricular asynchrony, though other kinds of asynchrony, such as intraventricular asynchrony are also possible.

The stimulation of either the region near the His bundle 16 or the para-Hisian region 17 achieves two simultaneous ends. Three pacing modes are available, (a) dedicated DDD pacing (always ON) with a short AV interval, (b) on-demand according to QRS width (the latter parameter can be automatically triggered when QRS is wider than 100 msec), and (c) on-demand according to QRS width, manually compared with an averaging template. There is a programmable pacing duration, whose window is also programmable from three to ten beats. The modes enable the QRS width to be analyzed and the proper type of pacing provided, as further described infra with reference to FIG. 13.

In a further embodiment, as Brugada syndrome is not present at all times, but instead appears and disappears as the conditions of the patient change, the presence of the Brugada syndrome electrocardiographic pattern can be sensed in an algorithmic way that enables stimulation delivery only when necessary, after an appropriate AV interval; ventricular stimulation is triggered upon the sensing of the atrial depolarization followed by a waiting period that constitutes the longest practicable interval that avoids bringing back the Brugada syndrome electrocardiographic pattern.

Figure 4:
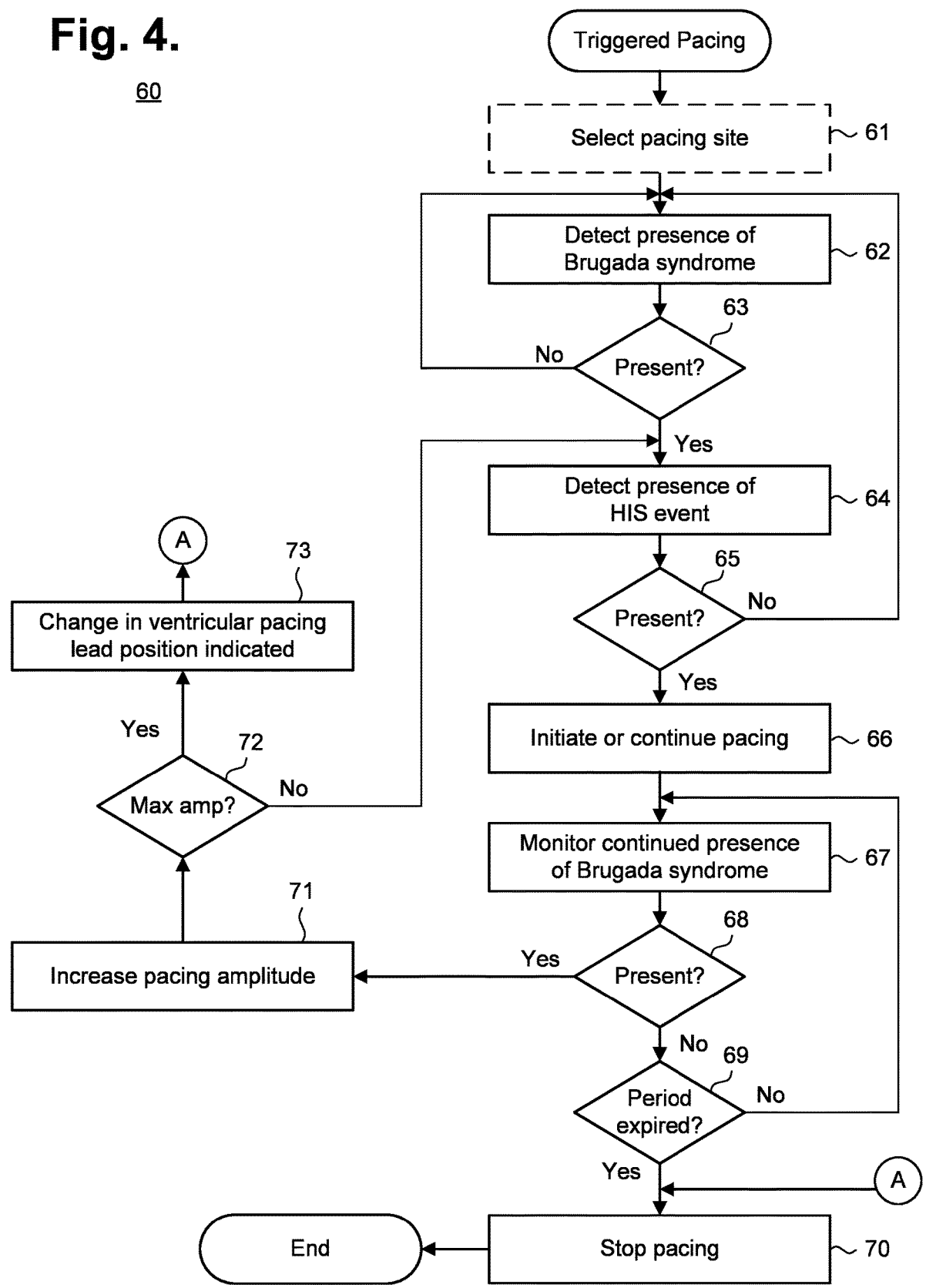
FIG. 4 is a flow diagram showing a method for treating Brugada syndrome through triggered pacing in accordance with one embodiment.

The twofold aim of detecting the presence of Brugada syndrome and bypassing the syndrome's defects can be provided by delivering cardiac episode-focused stimuli in the region near the His bundle 16 or para-Hisian region 17. FIG. 4 is a flow diagram showing a method 60 for treating Brugada syndrome through triggered pacing in accordance with one embodiment. The method 60 provides an algorithm for initiation of the pacing device, informing the physician of incorrect lead position, as appropriate, optimizing the pacing voltage, and deciding on whether to continue the ventricular stimulation upon the presence of Brugada syndrome physiology. The method 60 is operable on an implantable CRM device 19 under programmatic control, such as program code executable as a series of process or method modules or steps by the device's control circuitry, as described supra with reference to FIG. 1.

In a further embodiment, in addition to providing pacing through the pacing electrodes 23 in the region near the His bundle 16 or para-Hisian region 17, the implantable CRM device 19 can also wirelessly communicate with an external electrocardiographic system, as further described infra with reference to FIG. 11, which can sense whether the physiology indicative of the presence of Brugada syndrome is exhibited in the patient's electrocardiogram. By collaborating with the external electrocardiographic system, energy consumption of the implantable CRM device 19 can be minimized by limiting the amount of ventricular pacing delivered to the patient 10. The external electrocardiographic system helps the implantable CRM device 19 to avoid situations of creating a propagation wave front with inferior hemodynamic and functional efficacy in comparison to a normal propagation wave front, for instance, due to less than optimum lead positioning. In a still further embodiment, the method 60 is operable on a transiently-introduced electrophysiology catheter 190, in conjunction with an external pulse generator 191, such as used to induce ventricular arrhythmias during EPS.

Figure 15:
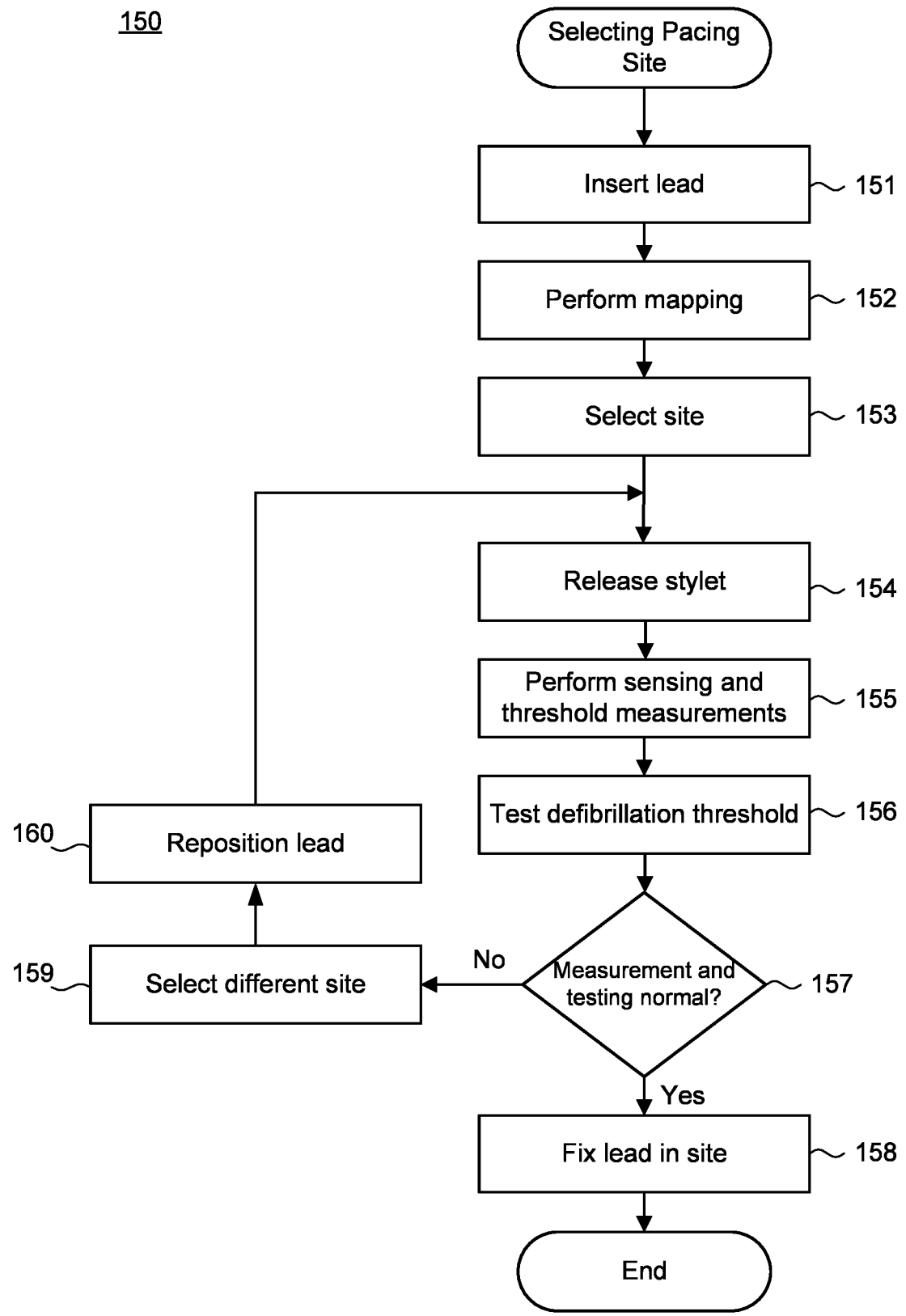
FIG. 15 is a flow diagram showing a routine 150 for selecting a site for delivering therapeutic stimulation by the pacing electrode in the region near the His bundle or the para-Hisian region for use in the methods of FIGS. 4 and 5 in accordance with one embodiment.

Optionally, if the therapeutic electrical stimulation delivered by the CRM device 19 does not include at least two single-phased superimposed waveforms of opposite polarity with respect to the indifferent electrode, a site for delivering therapeutic stimulation by the pacing electrode is selected in the region near the His bundle 16 or the para-Hisian region 17 (step 61), as further described below with reference to FIG. 15. The selection is typically performed during the implantation of the CRM 19, though other times to perform the selection are possible. During the selection, pacing that includes only waveforms of the same polarity is applied through the electrode 23, 25 to a plurality of potential pacing sites, and a level of asynchrony associated with each of the pacing sites is quantified, such as described above with reference to FIG. 1. Of the sites that are evaluated, the pacing site with the lowest measured asynchrony level is selected as the site where the electrode 23 is positioned for delivering pacing during treatment.

Once the CRM device 19 is installed, the patient's physiology is monitored to detect the presence of Brugada syndrome (step 62). Detection can be performed by first sensing cardiac physiology through the sensing amplifiers 34 and then providing the physiology to the external electrocardiographic system, as further described infra with reference to FIG. 11, which algorithmically identifies physiology indicative of a presence of Brugada syndrome in the patient 10. Alternatively, the detection can be performed by the sensing amplifiers 34 and the control circuitry of the implantable CRM device 19. If the syndrome is not present (step 62), no further action need be undertaken and, at later points in time, the presence of Brugada syndrome is again repeatedly detected (step 61).

Upon a finding of the presence of Brugada syndrome in the patient 10 (step 63), the patient's physiology is monitored to detect an event, specifically, propagation of an activation wave front proceeding from the AV node 36 of the patient's heart, either in region near the His bundle 16 or para-Hisian region 17 (step 64), as applicable. The detection can be performed by the sensing amplifiers 34 and the control circuitry of the implantable CRM device 19. If present (step 65), electrical stimulation therapy is delivered from the pulse generator output circuitry 33 (step 66), which initiates pacing at an AV delay triggered by atrial event sensing in the region near the His bundle 16 or para-Hisian region 17, or 50 msec, whichever is lower, at a pacing amplitude of about 1.2 times threshold. If detection is being performed using a transiently-introduced electrophysiology catheter, the same catheter can also be used to stimulate the region. Pacing is timed to be delivered substantially coincident to the arrival of the atrial event to the His bundle 16 or para-Hisian region 17. A few microseconds delay can occur between the arrival of the activation wave front and the initiation of delivery of electrical stimulation to the region. However, from the standpoint of cardiac myocytes, the delay is de minimus and the electrical stimulation is received simultaneously as part of the activation wave front timed to the waveform of the atrial activation.

Pacing continues for a predetermined period of time. The pacing will be maintained for 80 to 99% of the time, as physician-programmable due to its patient dependence, to enable for windows of time with no pacing, to verify if the pattern remains in the absence of pacing or that the syndrome has satisfactorily resolved due to a favorable change in the substrate of the patient's heart. Pacing is continued for a therapy interval that the health care personnel adjusts to the actual clinical substrate of the patient being treated. In the rare case of a patient in which the Brugada syndrome resolves in a spontaneous manner, the health care personnel may program a long interval, whereas a short interval may be more appropriate for a patient in which Brugada syndrome manifestations tend to appear for only brief periods of time.

During pacing, the patient's physiology is periodically monitored to detect the presence of Brugada syndrome (step 67), in the same manner described supra, which also confirms that the pacing amplitude of 1.2 times threshold is sufficient to suppress the Brugada syndrome manifestations. If the syndrome is still present (step 68), the pacing amplitude is increased (step 71) until a programmable maximum amplitude of 15 to 30 volts is reached, in which case the physician is advised to review the position of the lead. Thus, if the maximum allowable pacing amplitude has been reached (step 72), a problem likely exists and a change in ventricular pacing lead position is indicated (step 73), after which pacing stops (step 70) and the method ends.

Otherwise, if the syndrome is not present, yet the predetermined period of time for pacing has not yet expired (step 69), the patient's physiology is again monitored to detect the presence of Brugada syndrome (step 67), as described supra. However, if the predetermined period of time for pacing has expired (step 69), pacing is stopped (step 70) and the method ends.

Figure 5:
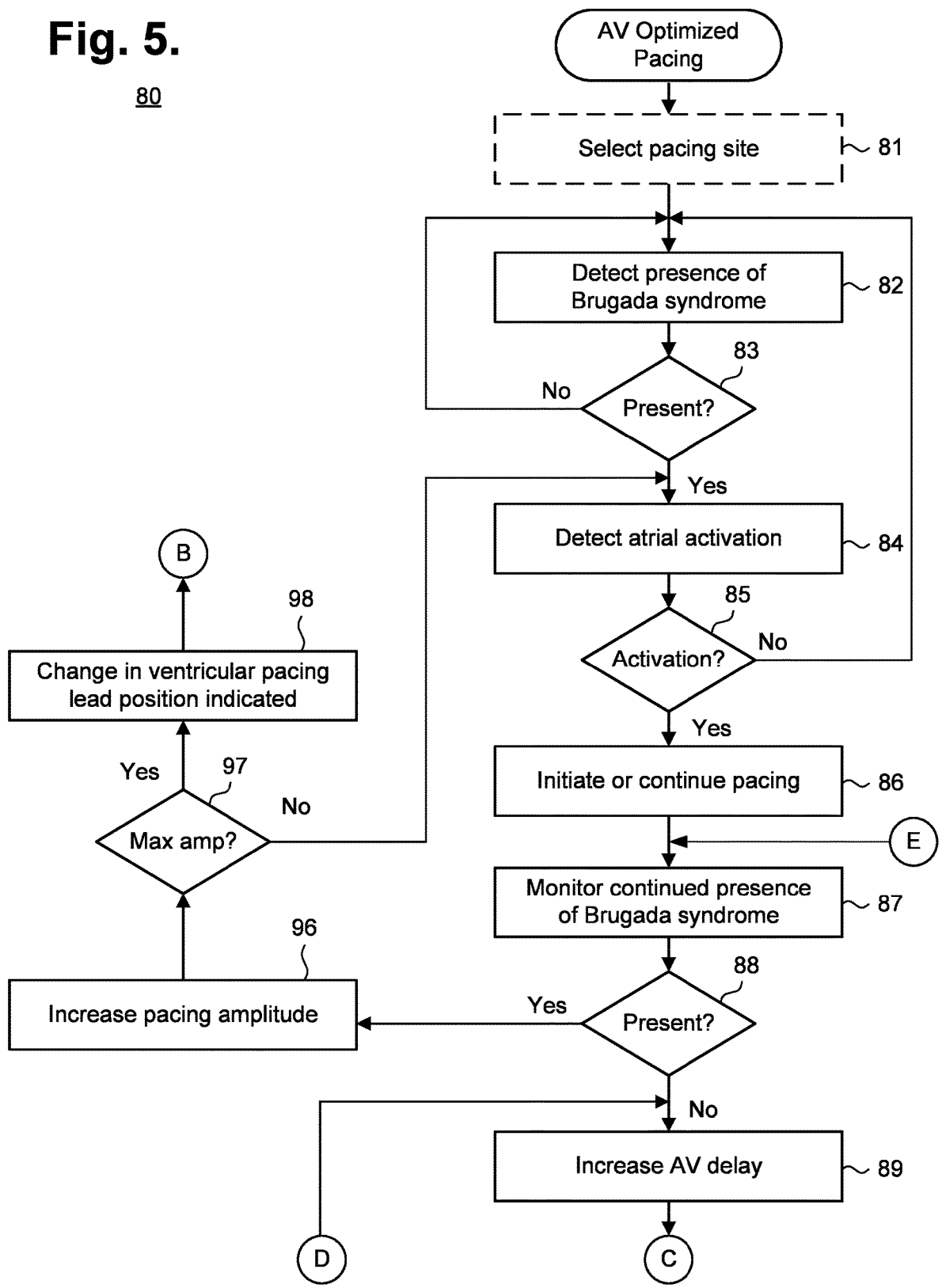
FIG. 5 is a flow diagram showing a method for treating Brugada syndrome through optimized atrioventricular nodal pacing in accordance with a further embodiment.

The foregoing method relied on the direct early detection of the arrival of the activation wave front to the region near the His bundle 16 or para-Hisian region 17. Alternatively, atrial activity can be sensed in lieu of or in addition to His or para-Hisian events. FIG. 5 is a flow diagram showing a method 80 for treating Brugada syndrome through optimized atrioventricular nodal pacing in accordance with a further embodiment. The method 80 provides an algorithm for initiation of the pacing device, informing the physician of incorrect lead position, as appropriate, optimizing AV delay and pacing voltage, and deciding on whether to continue the ventricular stimulation upon the presence of Brugada syndrome physiology. The method 80 is operable on an implantable CRM device 19 under programmatic control, in wireless communication with an external electrocardiographic system, or on a transiently-introduced electrophysiology catheter 190, in conjunction with an external pulse generator 191, as described supra.

Parts of the method are the same as performed for the direct early activation wave front detection method. Optionally, if the therapeutic electrical stimulation delivered by the CRM device 19 does not include at least two single-phased superimposed waveforms of opposite polarity with respect to the indifferent electrode, a site for delivering therapeutic stimulation by the pacing electrode is selected in the region near the His bundle 16 or the para-Hisian region 17, as further described below with reference to FIG. 15 (step 81). The selection is typically performed during the implantation of the CRM 19, though other times to perform the selection are possible. During the selection, pacing that includes only waveforms of the same polarity is applied through the electrode 23, 25 to a plurality of potential pacing sites, and a level of asynchrony associated with each of the pacing sites is quantified, such as described above with reference to FIG. 1. Of the sites that are evaluated, the pacing site with the lowest measured asynchrony level is selected as the site where the electrode 23 is positioned for delivering pacing during treatment.

Following the implantation, the patient's physiology is monitored to detect the presence of Brugada syndrome (step 82). Detection can be performed by first sensing cardiac physiology through the sensing amplifiers 34 and then providing the physiology to the external electrocardiographic system, which algorithmically identifies physiology indicative of a presence of Brugada syndrome in the patient 10. Alternatively, the detection can be performed by the sensing amplifiers 34 and the control circuitry of the implantable CRM device 19. If the syndrome is not present (step 83), no further action need be undertaken and, at later points in time, the presence of Brugada syndrome is again repeatedly detected (step 82).

Upon a finding of the presence of Brugada syndrome in the patient 10 (step 83), the patient's physiology is monitored to detect an atrial activation event (step 84). The detection can be performed by the sensing amplifiers 34 and the control circuitry of the implantable CRM device 19. If an atrial activation event is detected (step 85), electrical stimulation therapy is delivered from the pulse generator output circuitry 33 (step 86), which initiates pacing at an AV delay triggered by the atrial activity sensing; atrial pacing, where the patient 10 requires atrial pacing, that is equal to 50% of the previous interval between atrial and ventricular sensing; or 50 msec, whichever is lower, at a pacing amplitude of about 1.2 times threshold. Pacing continues for a predetermined period of time.

During pacing, the patient's physiology is periodically monitored to detect the presence of Brugada syndrome (step 87), in the same manner described supra, which also confirms that the pacing amplitude of 1.2 times threshold is sufficient to suppress the Brugada syndrome manifestations. If the syndrome is still present (step 88), the pacing amplitude is increased (step 96) until a programmable maximum amplitude of 15 to 30 volts is reached, in which case the physician is advised to review the position of the lead. Thus, if the maximum allowable pacing amplitude has been reached (step 97), a problem likely exists and a change in ventricular pacing lead position is indicated (step 98), after which pacing stops (step 95) and the method ends.

Once the lowest voltage at which the manifestations of Brugada syndrome are removed has been found, the atrioventricular AV delay is increased. The delay between atrial activation events is optimized to reflect the longest AV delay permitted without affecting the reappearance of the Brugada syndrome manifestations. The AV delay is fine-tuned by continually monitoring the patient's physiology to detect the presence of Brugada syndrome. Otherwise, if the syndrome is not present (step 88), the AV delay is increased (step 89). The AV delay is slowly increased in steps of one to 20 msecs, with 5 msecs being preferable, until the Brugada syndrome electrocardiographic pattern reappears. Following a period of pacing, the patient's physiology is once again monitored to detect the presence of Brugada syndrome (step 90), in the same manner described supra. If the syndrome is no longer present (step 91) and the maximum AV delay has not yet been reached (step 92), the AV delay is again increased (step 89). However, if the maximum AV delay has been reached without affecting the reappearance of the Brugada syndrome manifestations (step 92), the AV delay is shorted back to the previous AV delay (step 93) and pacing is continued for a therapy interval that the health care personnel adjusts to the actual clinical substrate of the patient 10 being treated. Using the longest AV delay that still removes the undesired effects of Brugada syndrome ensures that the optimal pre-load will be minimally affected by the stimulation, thus maintaining near normal hemodynamics in the heart. The pacing will be maintained for 80 to 99% of the time, as physician-programmable due to its patient dependence, to enable for windows of time with no pacing, to verify if the pattern remains in the absence of pacing or that the syndrome has satisfactorily resolved due to a favorable change in the substrate of the patient's heart.

If the predetermined period of time for pacing has expired (step 94), pacing is stopped (step 95) and the method ends.

Figure 6:
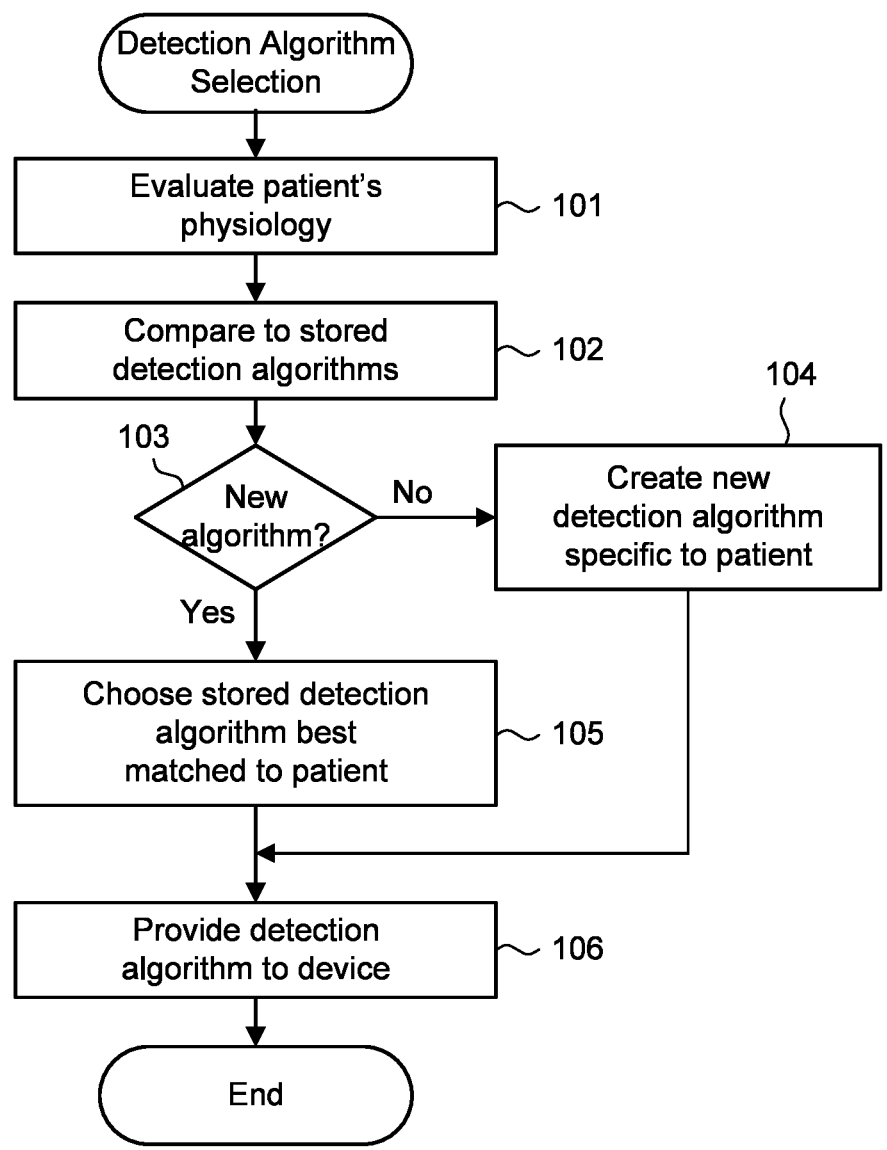
FIG. 6 is a flow diagram showing a method 100 for selecting an algorithm for detecting Brugada syndrome for use in conjunction with the methods of FIGS. 4 and 5.

As battery technology improves and processing power becomes less expensive in terms of cost and battery life, the algorithm to detect the presence of the Brugada syndrome electrocardiographic pattern could be internally implemented as part of the control circuitry of the implantable CRM device 19. FIG. 6 is a flow diagram showing a method 100 for selecting an algorithm for detecting Brugada syndrome for use in conjunction with the methods of FIGS. 4 and 5. To select an appropriate Brugada syndrome detection algorithm, the patient's physiology would first be evaluated (step 101), then compared to against a set of stored predefined algorithms (step 102). A new algorithm specific to the patient could be created from the physiology (step 105) if desired (step 104). Depending upon the cost tradeoffs of development, production, maintenance, regulatory compliance, and other factors at the time of production, an individualized algorithm could be created that maps for each patient the changes in the intracardiac electrocardiographic patterns that are detected with the implanted sensing electrodes 24, 26 to the presence or absence of the Brugada syndrome electrocardiographic pattern as registered by an external electrocardiographic system. Otherwise, a best matching detection algorithm could be chosen for the patient 10 (step 105), whether a standard "one size fits all" algorithm, an algorithm selected from a set of generic algorithms to cover different classes of patients, or other suitable form of detection algorithm.

Once selected, the detection algorithm can be provided to the implantable CRM device 19 (step 106), or to an external electrocardiographic system, external sensor, or programmer, if detection of Brugada syndrome is being performed transiently, such as during EPS. During use, the device will match the electrographic differences detected by the sensing electrodes 24, 26 with the Brugada syndrome electrocardiographic pattern specified in the detection algorithm for the patient 10.

In a still further embodiment, an individualized algorithm could be developed directly from the patient's physiology and automatically uploaded into the device used for Brugada syndrome detection. This approach would have the advantage of not limiting the set of parameters that would need to be adjusted to ensure an univocal match between the Brugada syndrome electrocardiographic pattern, as detected by an external ECG system, and by the internal algorithm in the implantable CRM device 19, or external device, as applicable. In addition, advances in signal processing would enable continual creation of improved detection algorithms, even after the device has already been implanted in the patient 10. Still other ways to formulate Brugada syndrome detection algorithms and to equip an implantable CRM device 19 or external device are possible.

The precise mechanism by which Brugada syndrome causes arrhythmias is unknown, but has been theorized to be due to transmural depolarization dispersion or transepicardial repolarization dispersion, which can lead to reentrant VTs in Phase 2. Brugada syndrome is characterized by alterations in several ion channels, and, in particular, changes in the sodium ion channel with overexpression of cardiac transient outward potassium current. These changes are mainly expressed in the epicardium with higher endo-to-epi repolarization gradients that facilitate the reentry mechanisms in polymorphic cells.

The cardiac stimulation delivered by the implantable CRM device 19, or external device, as applicable, used in treating Brugada syndrome compensates for electrical shifts in the balance of the voltage-dependent sodium, potassium and, eventually, calcium ion channels by applying a relatively intense electrical field. This electrical field facilitates normalizing those channelopathies, after which the electrocardiographic signs of Brugada syndrome disappear, along with the specter of its sudden death manifestation. To enable the following physician or health care provider to verify the disappearance of the electrocardiographic manifestations of Brugada syndrome, the cardiac stimulation must not be allowed to produce alterations in the electrocardiogram that could mask the signs typical of Brugada syndrome, for instance, the left ventricular bundle block image of right ventricular apical pacing. The normal conduction through the His-Purkinje system produces a fast, sequential, synchronous depolarization of the myocardial fibers, making the ventricular contraction more efficient. Consequently, the region near the His bundle 16 and the para-Hisian region 17 are ideal pacing sites for maintaining a normal activation pattern and enabling the verification of the disappearance of the Brugada syndrome electrocardiographic pattern.

A foregoing approach allows the generation of an activation wave front with near-normal ventricular depolarization and narrow QRS complexes in patients that already exhibit narrow basal QRS complexes. This type of activation wave front is well suited to eliminating the typical electrocardiographic signs of Brugada syndrome. Near-physiologic stimulation is delivered substantially simultaneously to atrial activation by using a "virtual electrode" that allows the creation of a stimulation field far stronger than a conventional electrode, which can correct the depolarization and conduction abnormalities present in Brugada syndrome. Moreover, this stronger stimulation field entrains areas that are farther away from the actual pacing site and can thereby overcome conduction disturbances. Thus, the use of this "virtual electrode" facilitates locating the pacing electrodes 23 in a location, specifically, the region near the His bundle 16 or para-Hisian region 17, that allows the health care operator to correct and effectively eliminate the Brugada syndrome electrocardiographic pattern, thereby obviating the need to perform complex electrophysiologic mapping procedures to define the stimulation site.

As delivered through the pacing electrodes 23, the high-energy stimulation at septal level modifies the electrocardiographic pattern in leads V1, V2, V3 through a "homogenizer effect" over the transmural epicardium/endocardium voltage gradient by acting on the involved voltage-dependent ionic channels and restoring an adequate epicardium/endocardium voltage ratio. There is also a homogenizing effect on the epicardium/endocardium repolarization dispersion, as well as in the intraepicardiac dispersion. The efficacy of the stimulation herein provided is theorized to be based on the fundamentally voltage-dependence, and consequently the "virtual electrode effect" at septum level, of the ionic sodium and potassium cellular channels. The stimulation could be modifying the altered charges in the epicardium area of the right ventricular outflow tract, which is close to the pacing sites used, that is, the region near the His bundle 16 and the para-Hisian region 17 of the heart 11. Alternatively, the "virtual electrode effect" may simply be due to the increase in the initial depolarization voltage, correcting and activating a small number (about one percent) of "slow" sodium channels, consequently eliminating the overexpression of the potassium current (Ito) evident in the electrocardiogram by elimination of the Brugada syndrome-typical pattern in leads V1, V2, V3. Last, a "tsunami effect" that modifies all the currents, including those of sodium, potassium and calcium in its various forms, may be triggered through the pacing and thus preventing reentry in Phase 2.

Figure 7A:
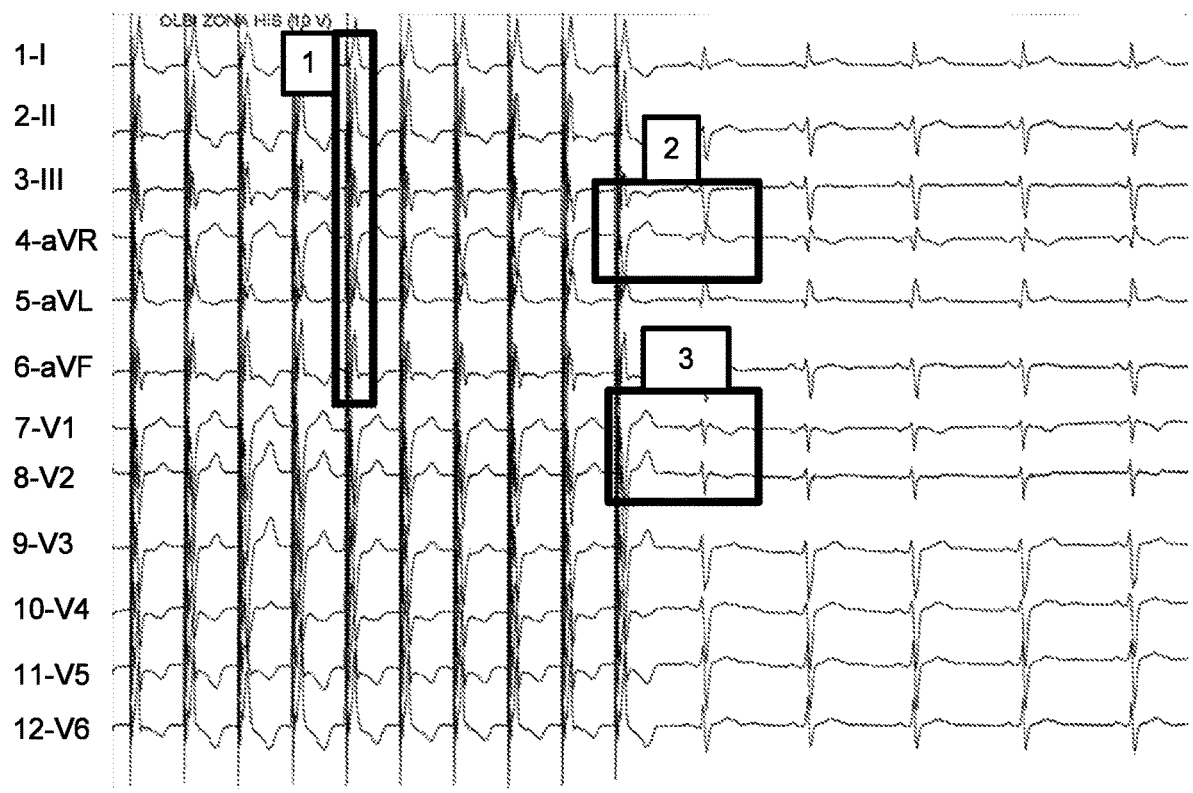
FIGS. 7A-B, 8A-B and 9A-B are graphs respectively showing, by way of example, 12-lead electrocardiograms for patients exhibiting Brugada syndrome following treatment through the methods of FIGS. 4 and 5 that involved application of at least two single-phased superimposed waveforms of opposite polarity with respect to the indifferent electrode.
Figure 7B:
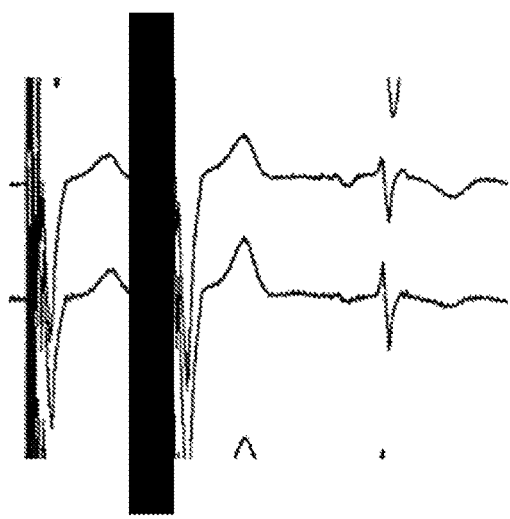

The waveforms and amplitudes used in the electrical stimulation delivered through the foregoing methods described supra with reference to FIGS. 4 and 5, by the implantable CRM device 19, or external device, as applicable, have been verified through clinical experiments to bypass the activation and conduction problems underlying the Brugada syndrome electrocardiographic pattern. FIGS. 7A-B, 8A-B and 9A-B are graphs respectively showing, by way of example, 12-lead electrocardiograms for patients exhibiting Brugada syndrome following treatment through the methods of FIGS. 4 and 5 that involved application of two single-phased superimposed waveforms of opposite polarity with respect to the indifferent electrode. Referring first to FIGS. 7A-B, the patient exhibiting manifestations of Brugada syndrome, as described supra with reference to FIG. 1, has undergone pacing in the para-Hsian region 17. Following therapy, several differences in cardiac profile can be noted, including a change of axis and elimination of left anterior fascicular block (box 1), a change in pattern in lead augmented vector right (aVR) (box 2), a disappearance of Brugada syndrome pattern in leads V1 and V2 (box 3), and a post-pacing reappearance of the syndrome's manifestations. No changes in J point or T wave in lead V3 are exhibited.

Figure 8A:
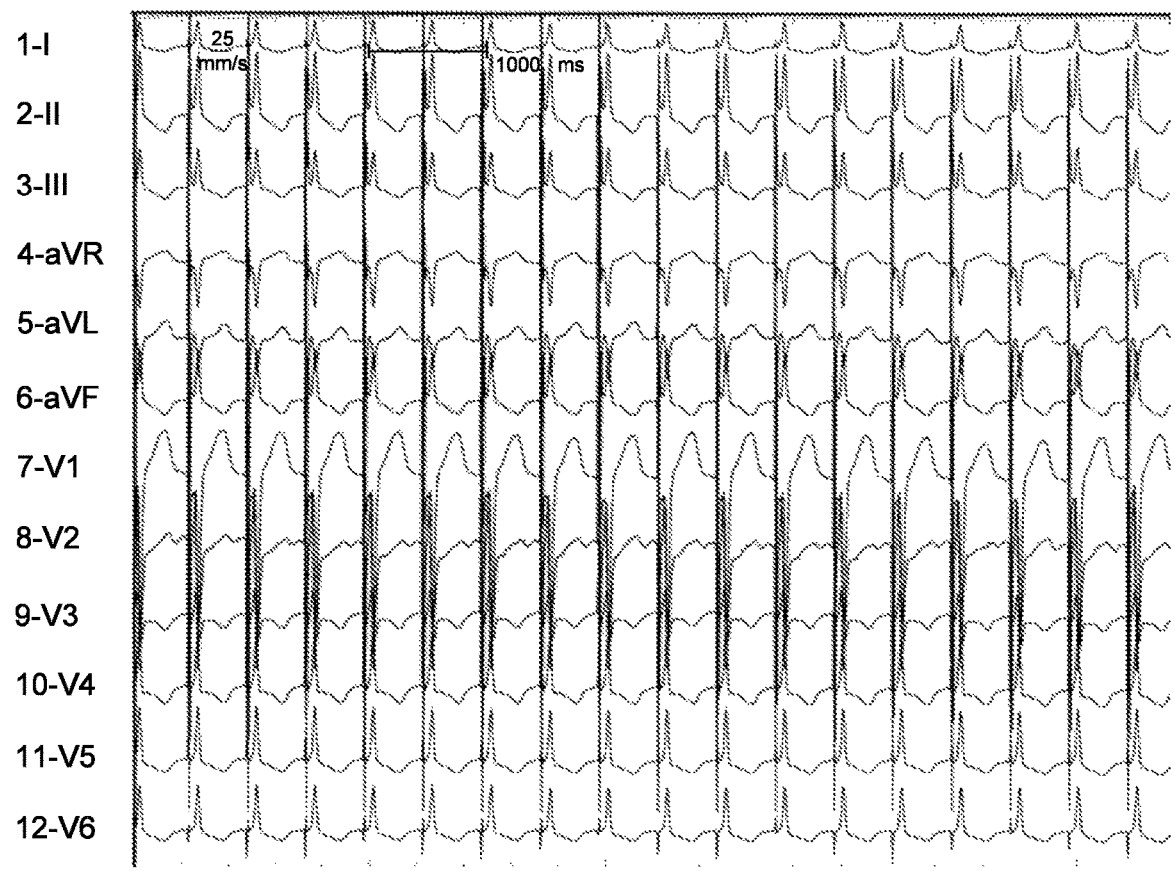
Figure 8B:
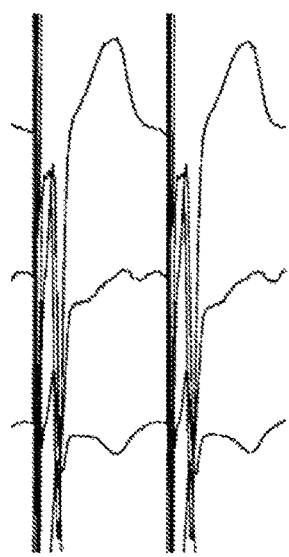

Referring next to FIGS. 8A-B, the patient exhibiting manifestations of Brugada syndrome, as described supra with reference to FIG. 2, has undergone pacing in the septal para-Hsian region 17. Following therapy, a change in pattern in aVR and a disappearance of Brugada syndrome pattern in leads V1 and V2 can be observed.

Figure 9A:
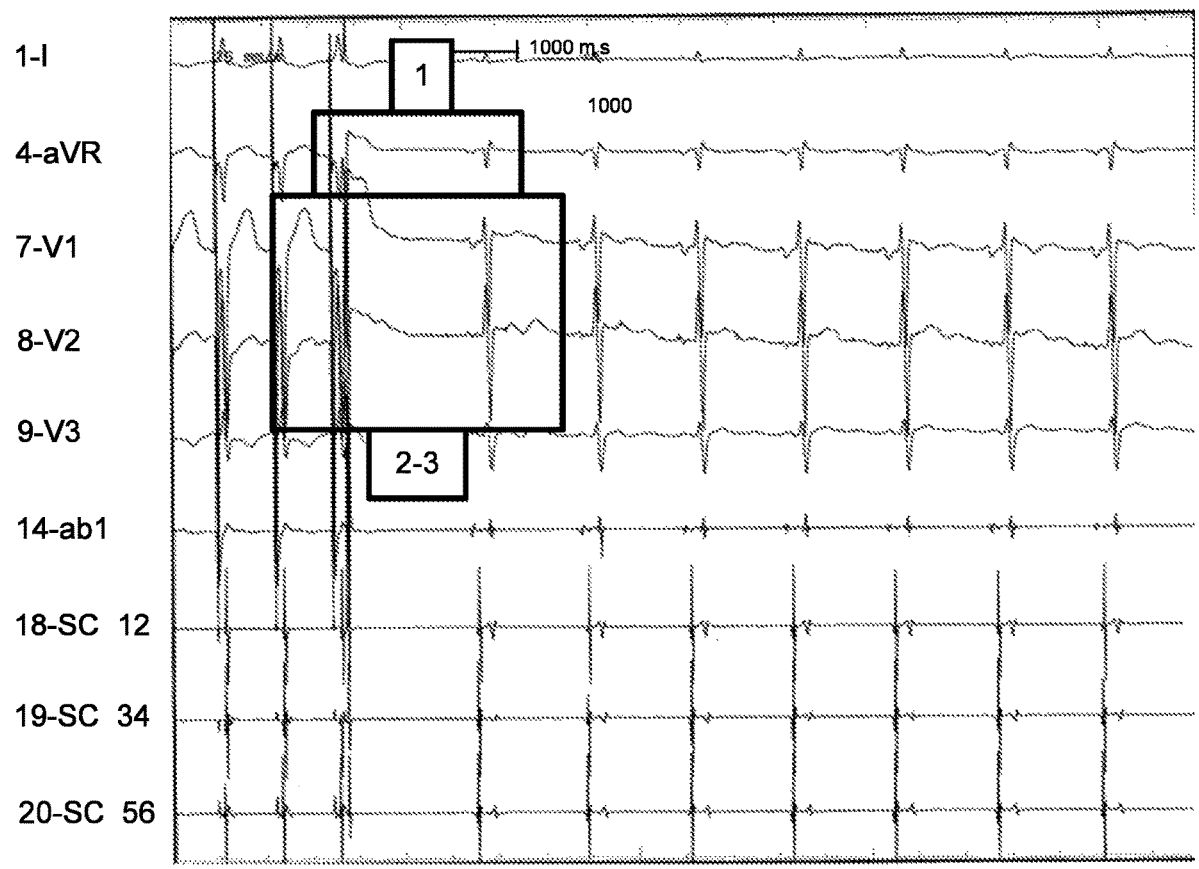
Figure 9B:
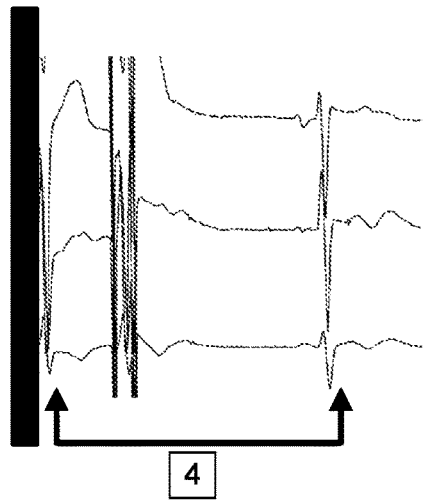

Finally, referring to FIGS. 9A-B, the same patient has again undergone pacing in the septal para-Hsian region 17. Following therapy, as before, a change in pattern in aVR (box 1) and a disappearance of Brugada syndrome pattern in leads V1 and V2 can be observed, as well as a partial reapparition (boxes 2-3) after a few beats and morphology the same as presented pre-pacing. No changes in J point or T wave in lead V3 are exhibited (box 4).

Figure 10A:
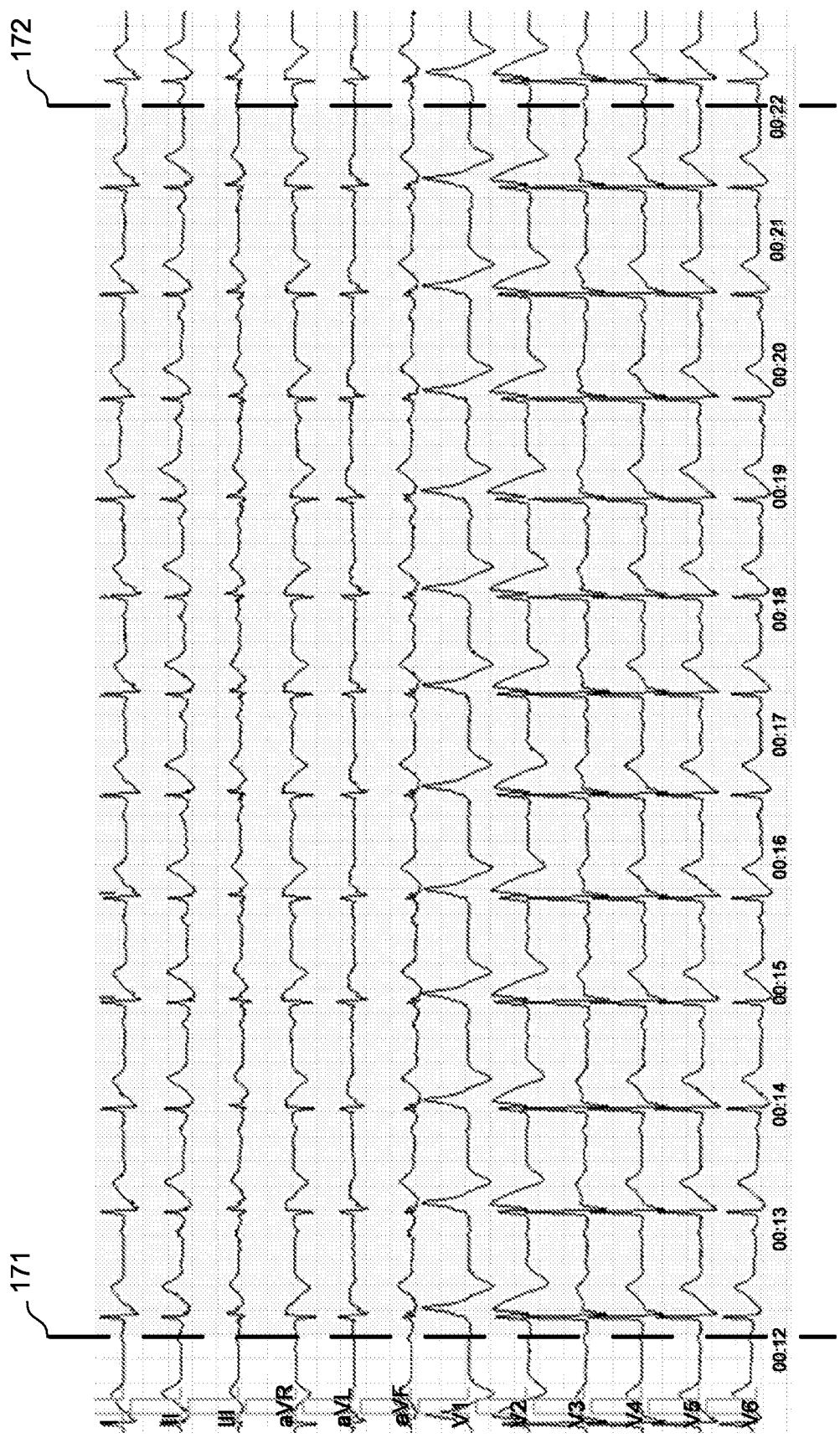
FIGS. 10A-10C are graphs respectively showing, by way of example, 12-lead electrocardiograms for a patient exhibiting Brugada syndrome before, during, and after application of therapeutic stimulation involving only waveforms of the same polarity by the CRM device.
Figure 10B:
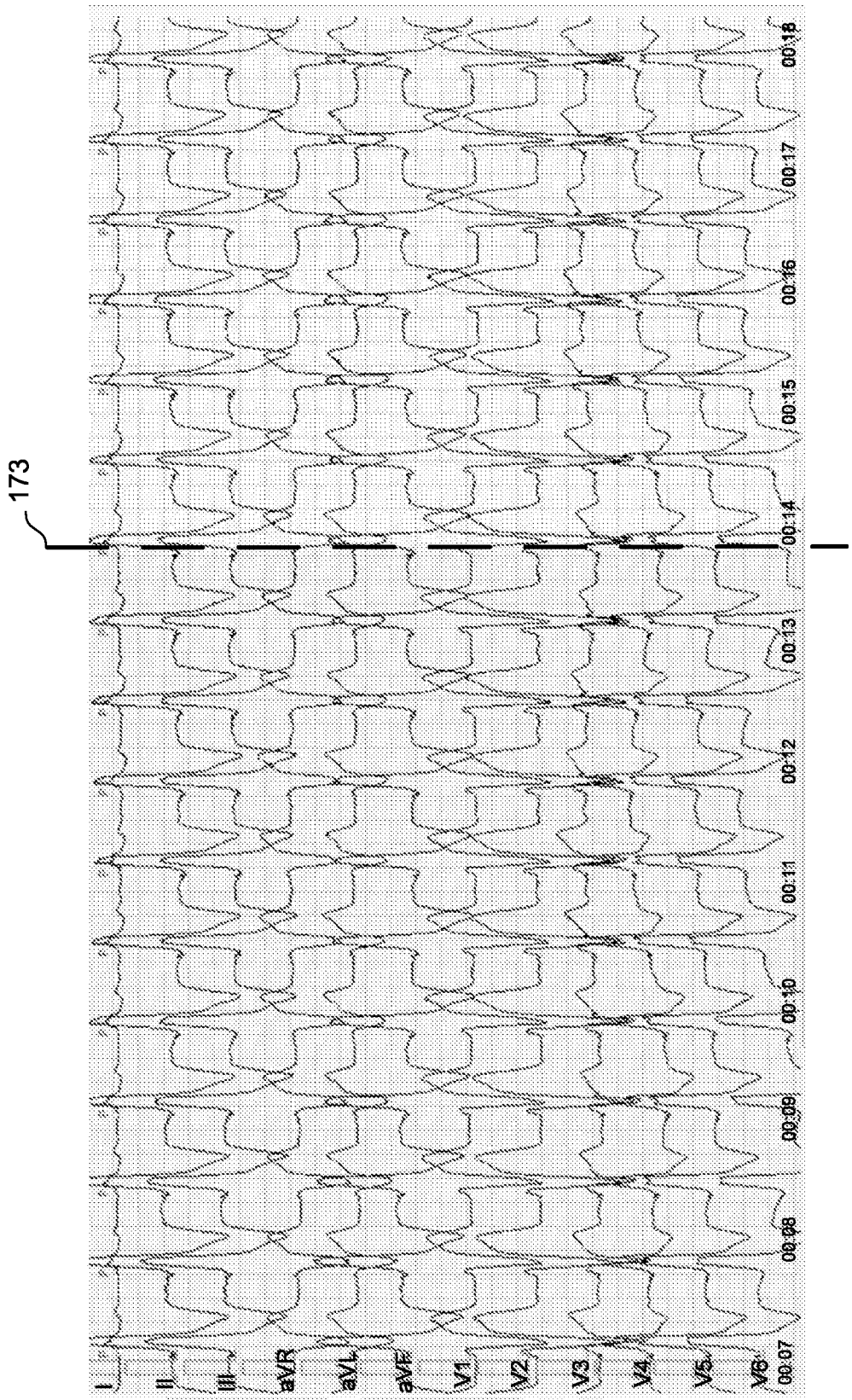
Figure 10C:
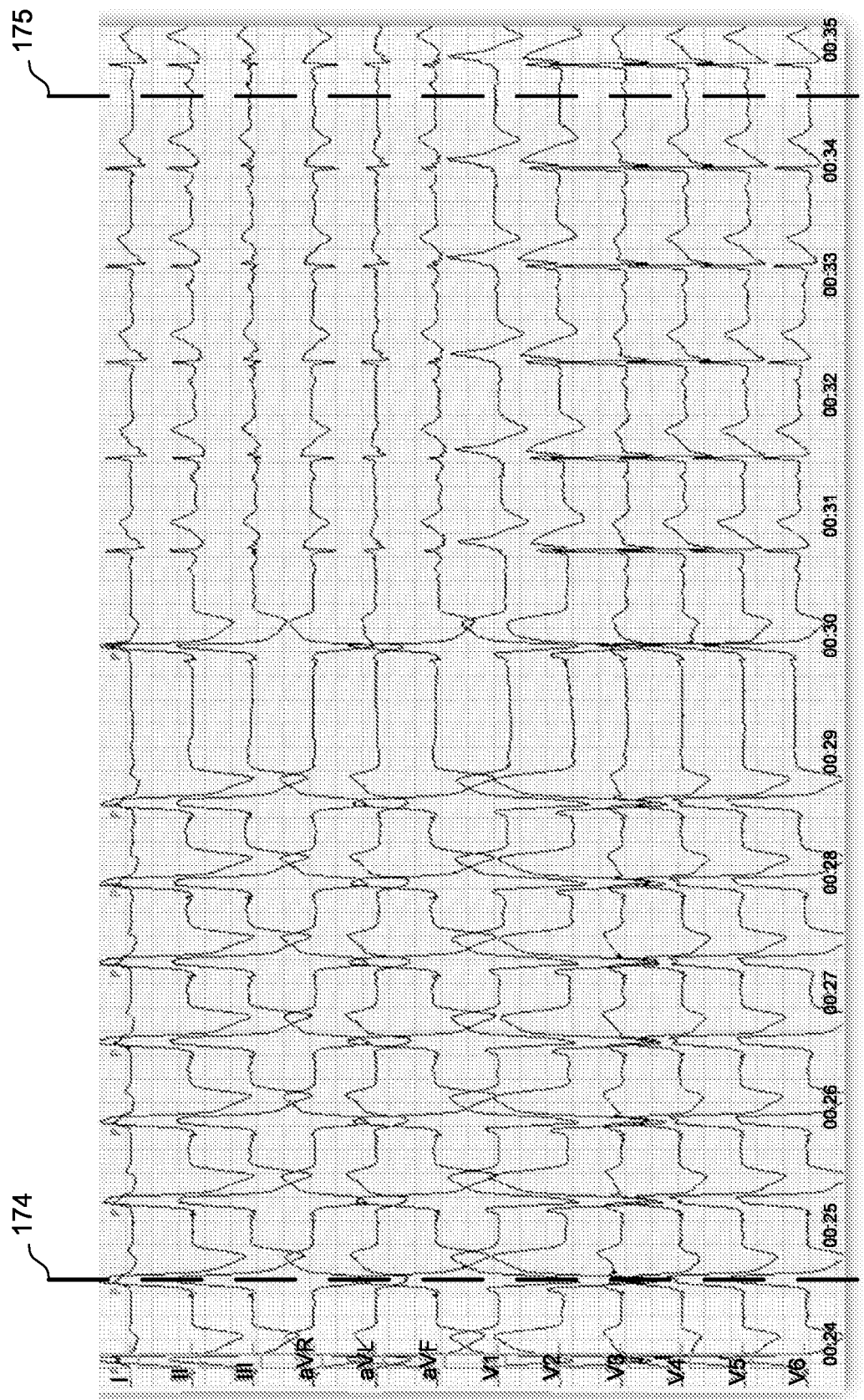

As mentioned above, normalization of the Brugada syndrome electrocardiographic pattern and the correction of the conduction and activation abnormalities caused by the Brugada syndrome can be achieved through therapeutic electrical stimulation that involves only pacing using waveforms of the same polarity, conventional pacing waveforms. The ability of the CRM device 19 to achieve this effect through pacing to a site selected based on the level of asynchrony associated with that site has been clinically verified. FIGURES IDA-10C are graphs respectively showing, by way of example, 12-lead electrocardiograms (ECG) for a patient exhibiting Brugada syndrome before, during, and after application of therapeutic stimulation involving only conventional pacing waveforms by the CRM device 19. As can be seen with reference to FIG. 10A, the patient is exhibiting Type 1 Brugada syndrome pattern prior to application of therapy, with the ECG of the patient when no stimulation is received being shown between the lines 171, 172. The Brugada pattern disappeared during application of electrical therapeutic stimulation, as can be seen with reference to FIG. 10B, where the ECG of the patient experienced during the application of the stimulation is shown to the right of the line 173. The CRM device 19 used to deliver the stimulation is an ICD, with the endocardial lead 19 being a screw-in defibrillation lead, with the pacing electrode 23 being placed in the Para-Hisian region. Following the termination of the para-Hisian stimulation, the Brugada pattern reappears, as can be seen with reference to FIG. 10C, where the ECG of the patient following cessation of the stimulation is shown between the lines 174, 175.

Figure 11A:
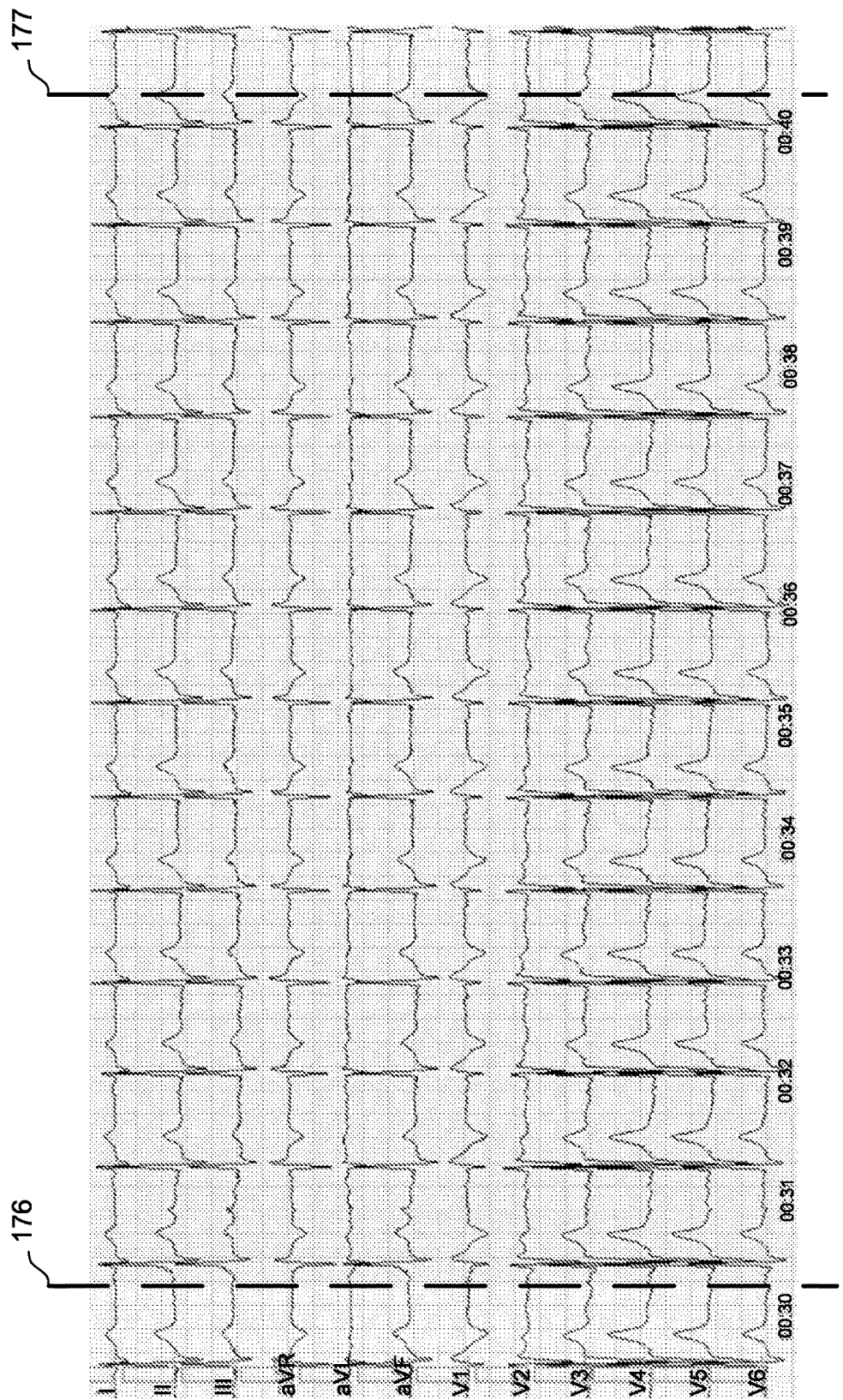
FIGS. 11A-11C, are graphs respectively showing, by way of example, 12-lead electrocardiograms for a second patient exhibiting Brugada syndrome before, during, and after application of therapeutic stimulation involving only waveforms of the same polarity by the CRM device.
Figure 11B:
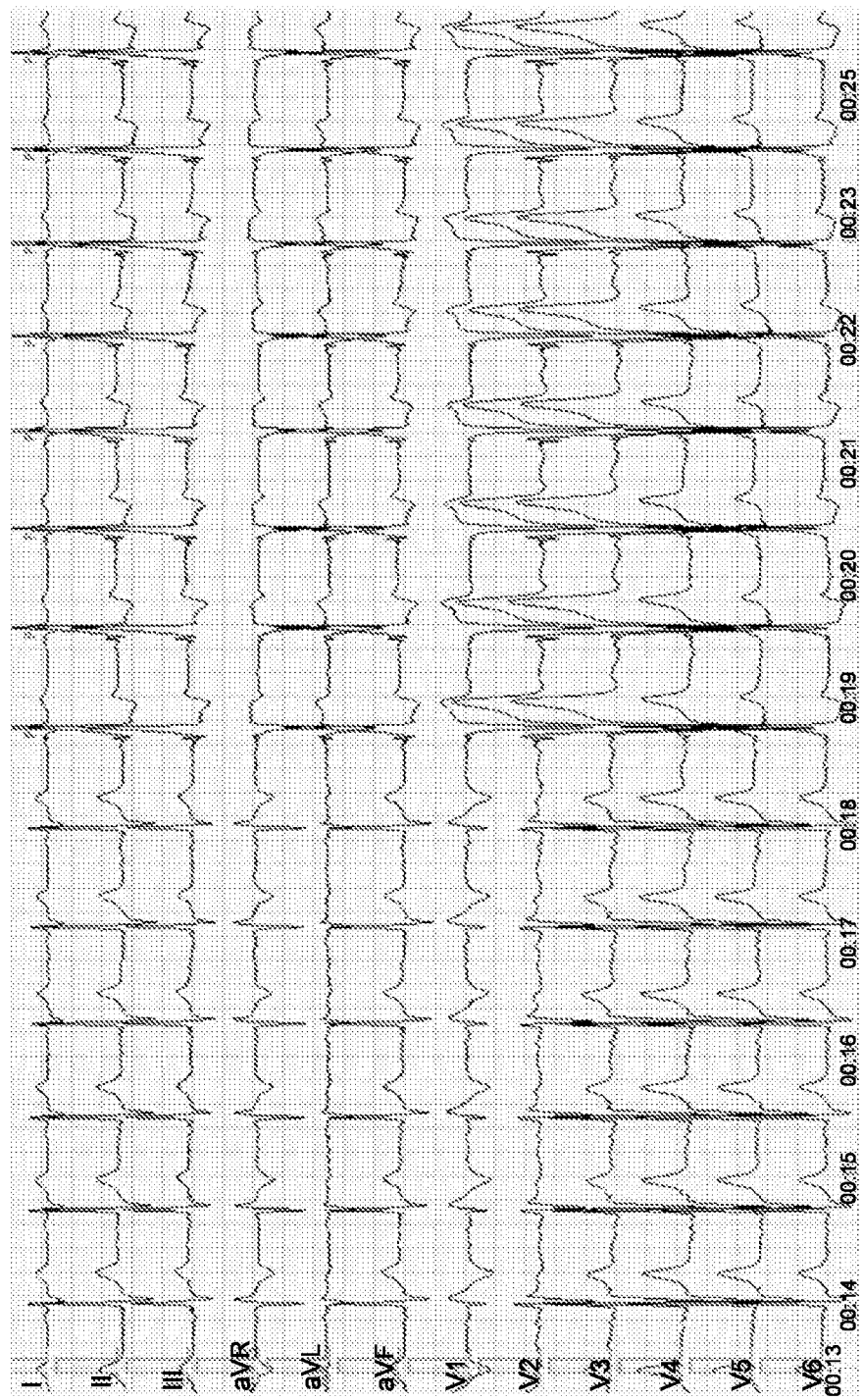
Figure 11C:
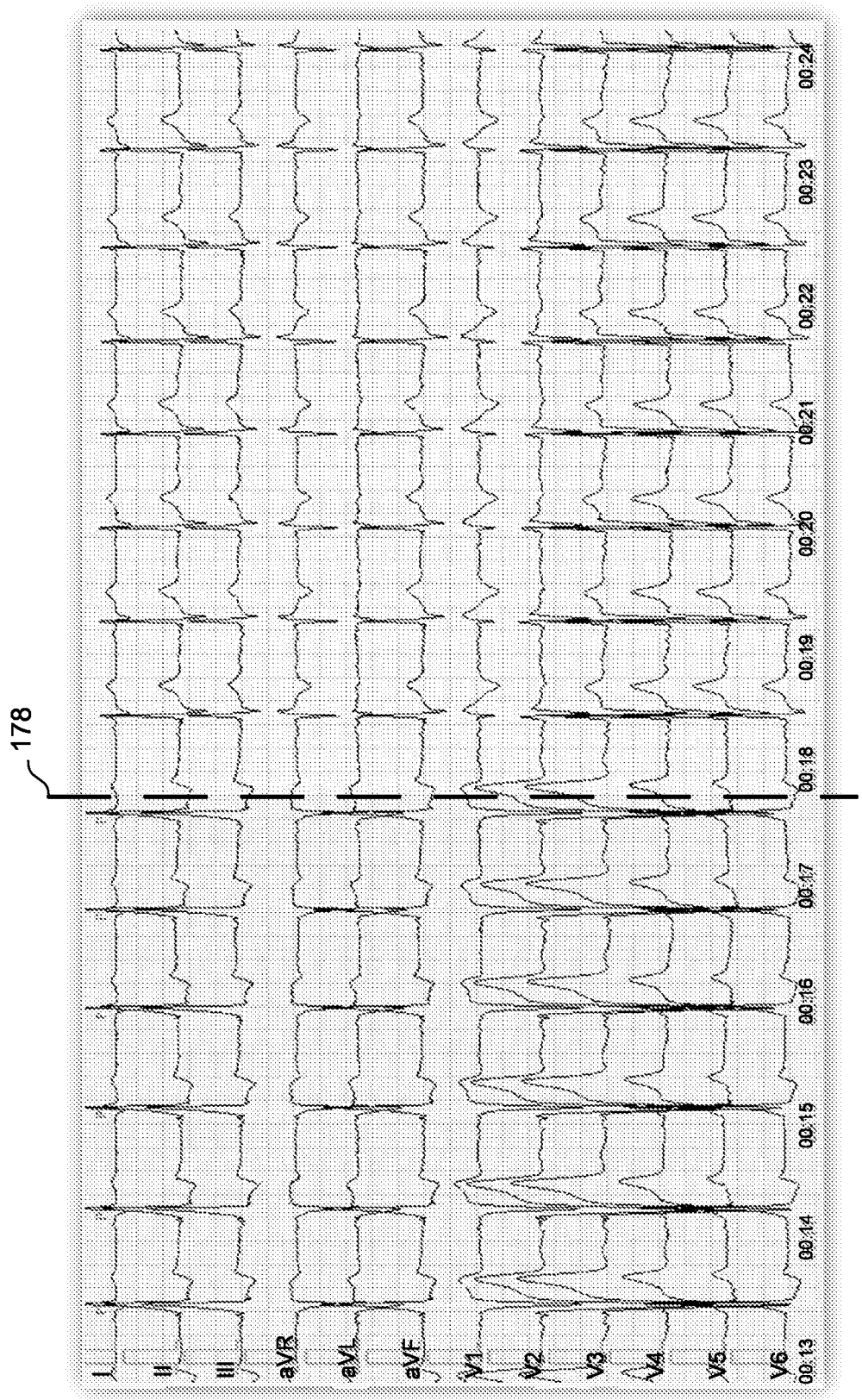

Similar results are shown with respect to FIGS. 11A-11C, which show by way of example, 12-lead electrocardiograms for a second patient exhibiting Brugada syndrome before, during, and after application of therapeutic stimulation involving only waveforms of the same polarity by the CRM device 19. As can be seen with reference to FIG. 11A, the patient exhibits Type 1 Brugada pattern prior to beginning of the stimulation, with the ECG of the patient when no stimulation is received being shown between the lines 176, 177. The application of the stimulation in the same manner as described above with reference to FIG. 10B causes the disappearance of the Brugada pattern, as seen with reference to FIG. 11B. The pattern reappears following the cessation of stimulation, as can be seen with reference to FIG. 11C, where the ECG of the patient following cessation of the stimulation is shown to the left of the line 178.

Figure 12A:
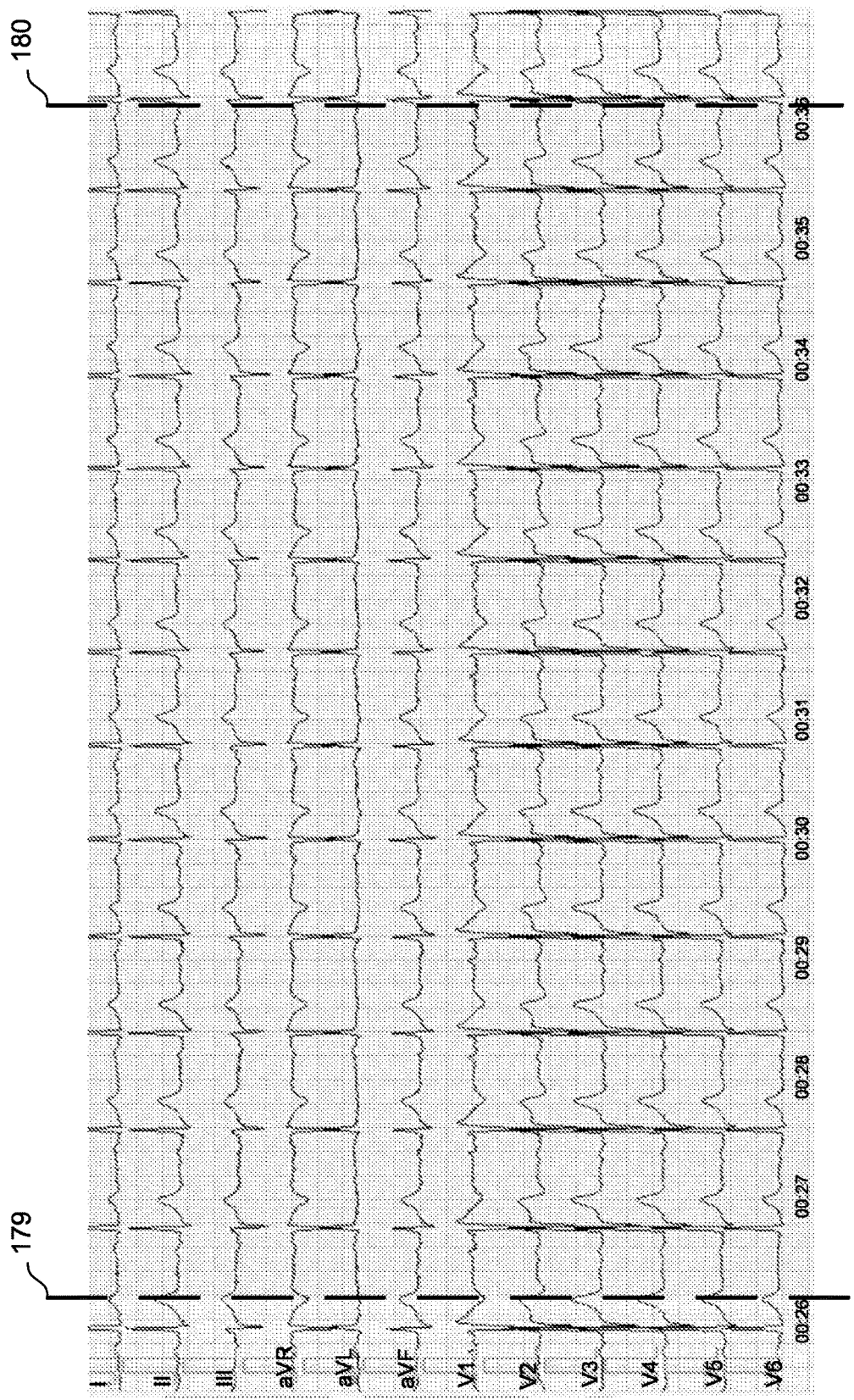
FIGS. 12A-12C, are graphs respectively showing, by way of example, 12-lead electrocardiograms a third patient exhibiting Brugada syndrome before, during, and after application of therapeutic stimulation by the CRM device.
Figure 12B:
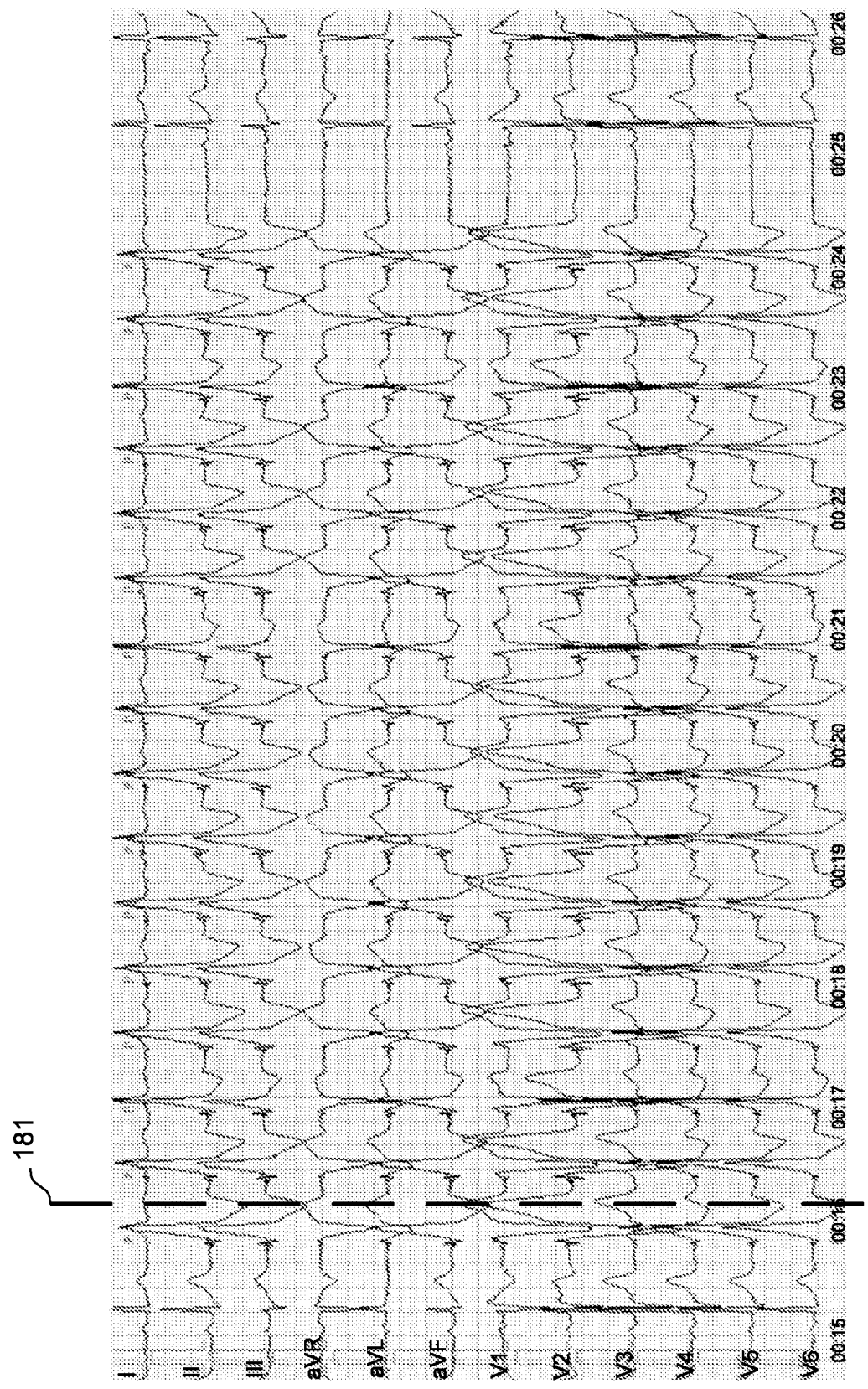
Figure 12C:
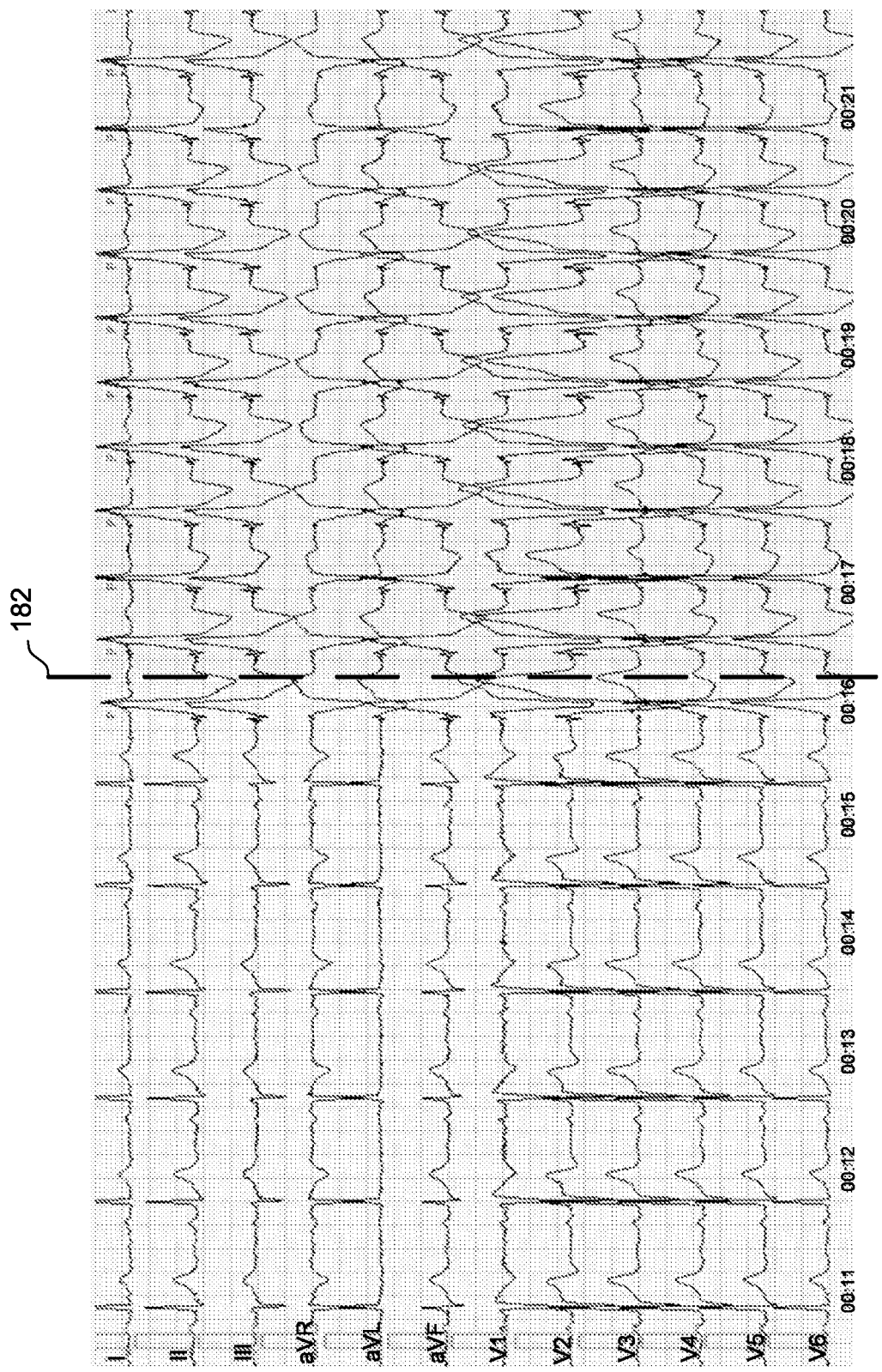

Likewise, FIGS. 12A-12C, which show by way of example, 12-lead electrocardiograms for a third patient exhibiting Brugada syndrome before and during application of therapeutic stimulation by the CRM device 19. As can be seen with reference to FIG. 12A, the patient exhibits Type 1 Brugada pattern prior to beginning of the stimulation As can be seen with reference to FIGS. 12B-C, the pattern disappears upon application of stimulation in the same manner as described above with reference to FIG. 10B, and reappears following cessation of stimulation, as can be seen with reference to FIG. 12C, where the ECG of the patient following cessation of the stimulation being shown between the lines 179, 180.

Figure 17:
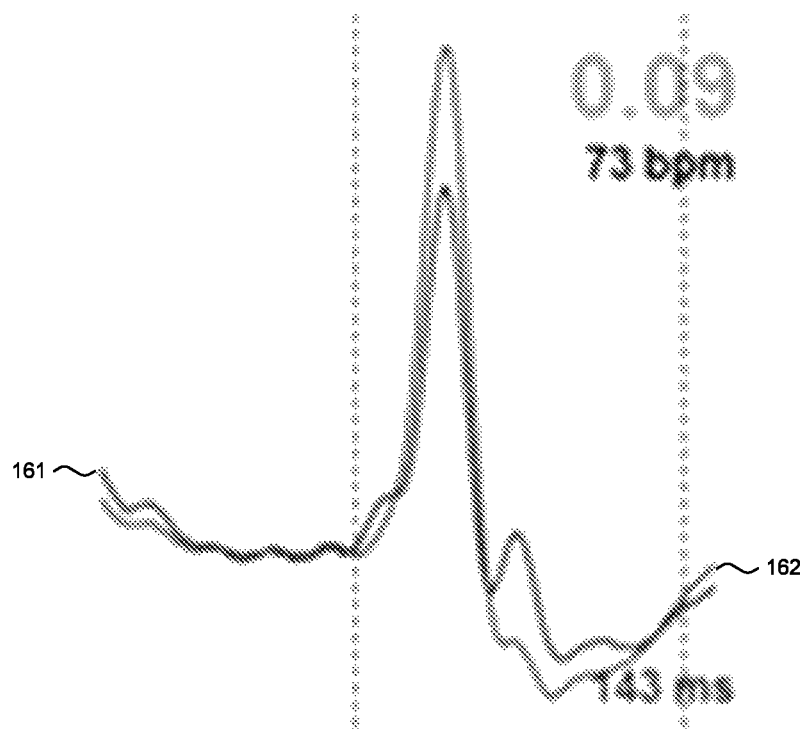
FIG. 17 shows surface ECG curves representing both left ventricle and right ventricle of the same patient whose 12-lead ECG is shown with reference to FIG. 10A and which are contemporaneous to the 12-lead ECG shown in FIG. 10A.
Figure 18:
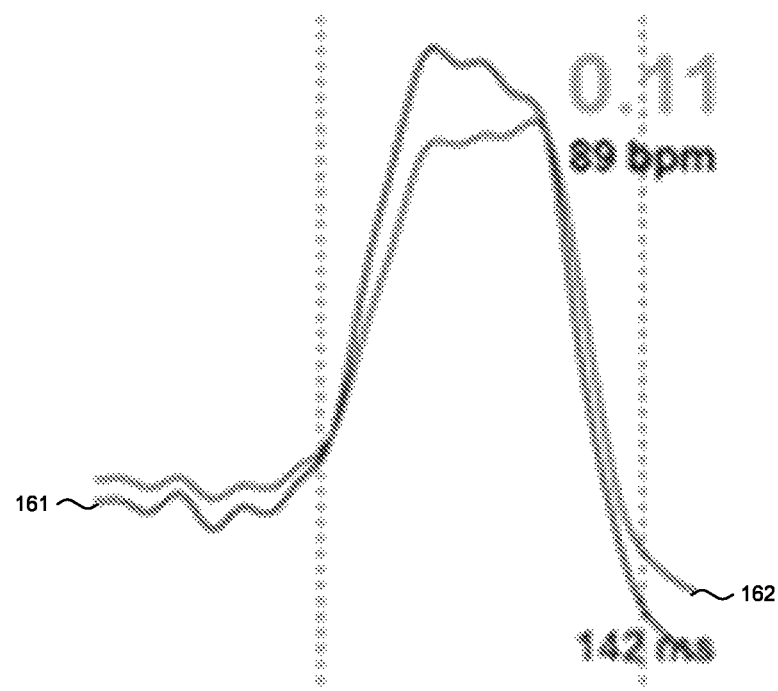
FIG. 18 shows surface ECG curves representing both left ventricle and right ventricle of the same patient whose 12-lead ECG is shown with reference to FIG. 10B and which are contemporaneous to the 12-lead ECG shown in FIG. 10B.

Further, the normalization of the Brugada syndrome achieved through pacing to a site selected based on associated cardiac electrical asynchrony has been empirically shown to be accompanied by a reduction in the patient's cardiac electrical asynchrony. FIG. 17 shows surface ECG curves representing both right ventricle 161 and left ventricle 162 of the same patient whose 12-lead ECG is shown with reference to FIG. 10A and which are contemporaneous to the 12-lead ECG shown in FIG. 10A. Both positive curves 161, 162 with QRS final portion delay without complete overlapping of two curves. An asynchrony area is evidenced. The asynchrony is reduced once the stimulation is applied, as can be seen with reference to FIG. 18. FIG. 18 shows surface ECG curves representing both right ventricle 161 and left ventricle 162 of the same patient whose 12-lead ECG is shown with reference to FIG. 10B and which are contemporaneous to the 12-lead ECG shown in FIG. 10B. As can be seen with reference to FIG. 18, during the application of the septal stimulation in the para-Hisian region, QRS final portion delay disappeared and a completely synchronous QRS is shown with two fully overlapping curves.

Figure 13:
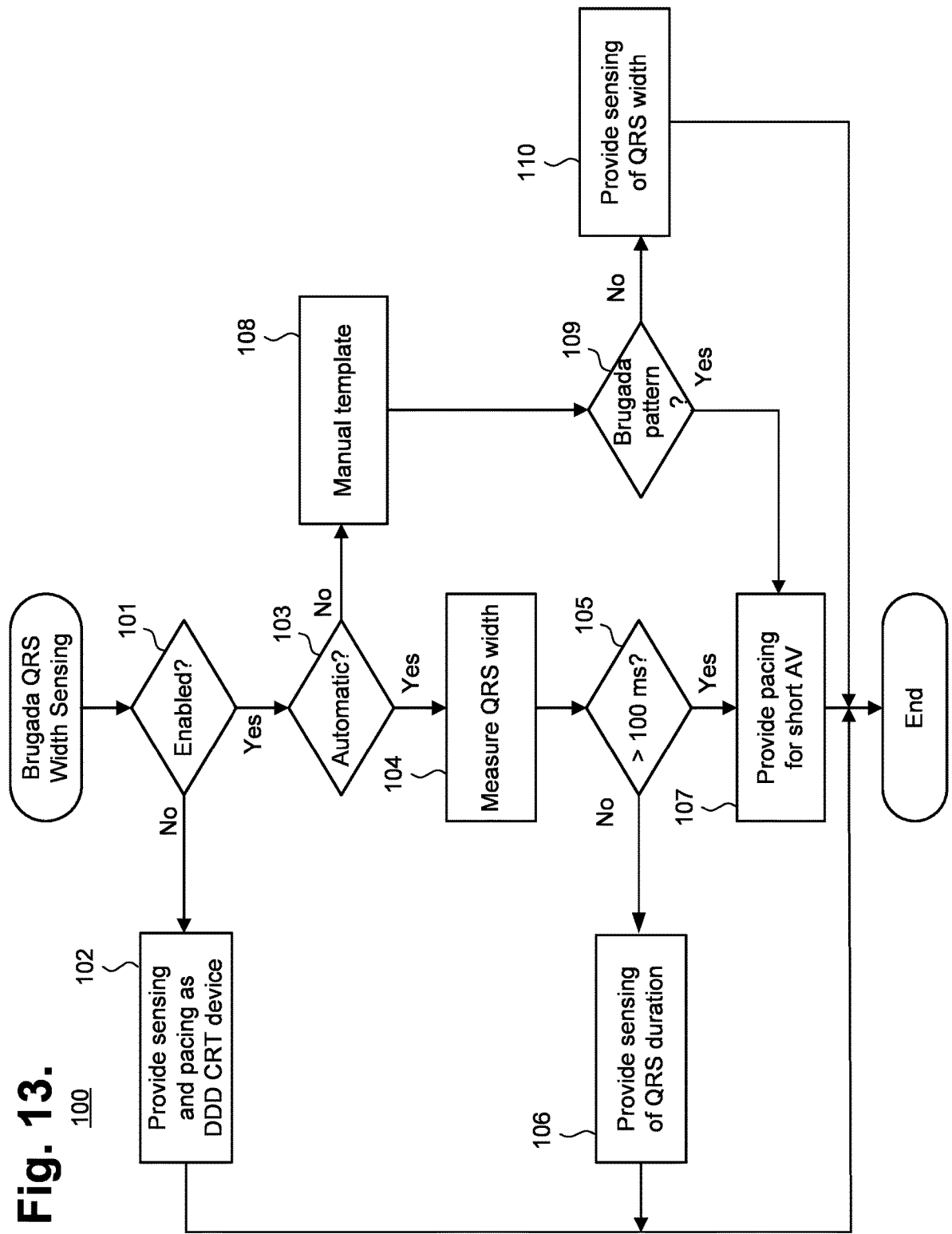
FIG. 13 is a flow diagram showing a method 100 for sensing QRS width for use in conjunction with the methods of FIGS. 4 and 5.

The three pacing modes enable the QRS width to be analyzed and the proper type of pacing provided. FIG. 13 is a flow diagram showing a method 100 for sensing QRS width for use in conjunction with the methods of FIGS. 4 and 5. The implantable CRM device 19 has at least three programmable parameters for pacing, which are para-Hisian, apex, or both para-Hisian and apex, and at least two values that reflect changes in the QRS width, which are coil-to-coil and ring-to-distal coil (programmable).

First, if Brugada syndrome QRS width sensing is not enabled (step 101), sensing and pacing are provided as for a DDD CRT device (step 102). Otherwise, if Brugada syndrome QRS width sensing is enabled (step 101) and the device is set to automatic mode (step 104), the QRS width is measured (step 104). If the QRS width is less than 100 msec (step 105), pacing for a short AV interval is provided (step 107). Otherwise, if the QRS width is equal to or greater than 100 msec (step 105), the QRS duration is sensed (step 106). If the device is not set to automatic mode (step 104), a manual adjustment template is used (step 108). If a Brugada syndrome pattern is apparent (step 109), pacing for a short AV interval is provided (step 107). Otherwise, if a Brugada syndrome pattern is not apparent (step 109), the QRS width is sensed (step 110).

Figure 14:
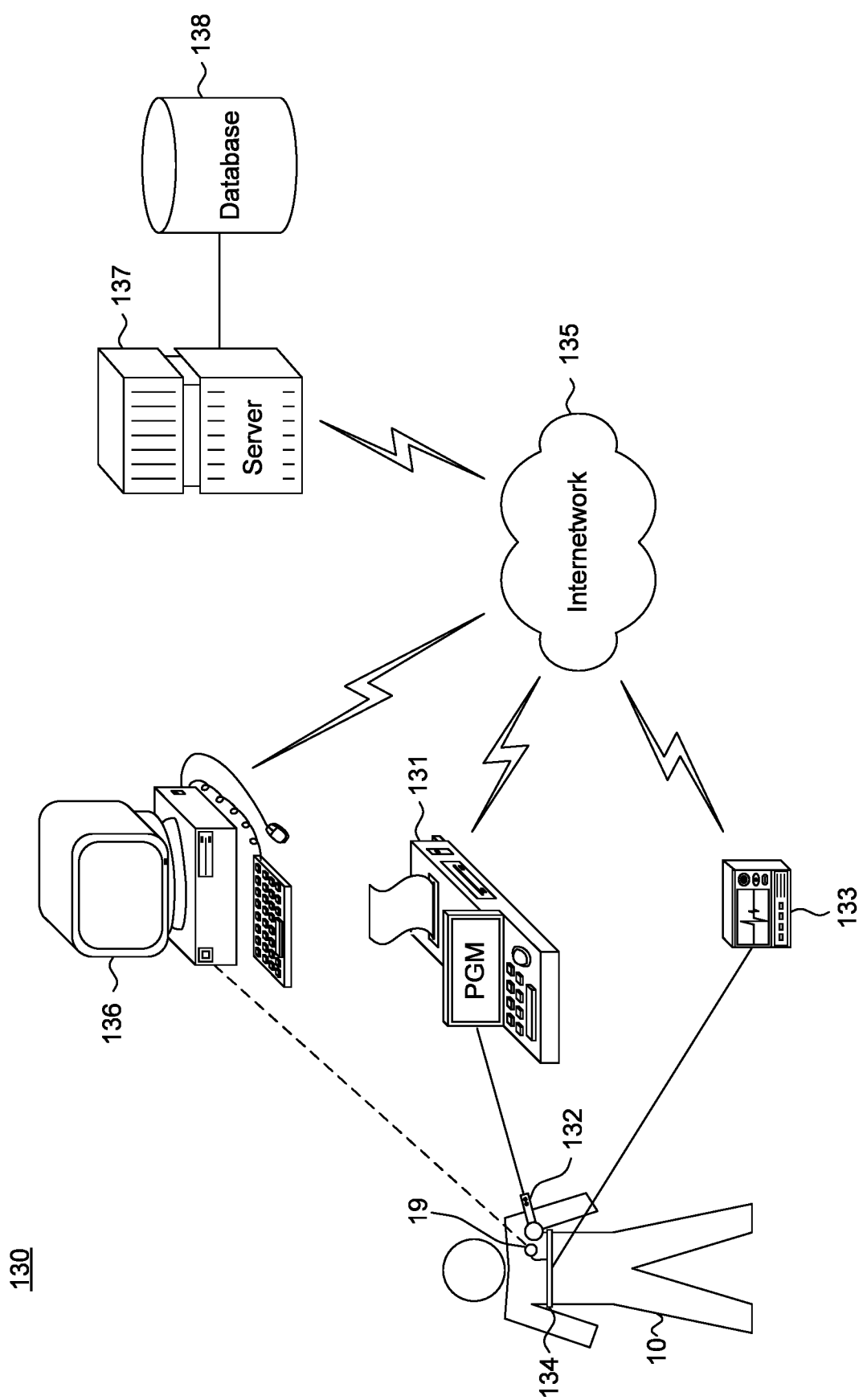
FIG. 14 is a functional block diagram showing a computer-implemented system for treating Brugada syndrome, in accordance with a further embodiment.

The pacing therapy can be delivered wholly in situ via an implantable CRM device 19 that performs sensing, detection algorithm analysis and pacing. Alternatively, the implantable CRM device 19 could be remotely coupled to an external electrocardiographic system that would collaboratively perform select aspects of the end-to-end treatment regime. FIG. 14 is a functional block diagram showing a computer-implemented system 130 for treating Brugada syndrome, in accordance with a further embodiment. The system 130 includes an external electrocardiograph machine 133, conventional external programmer 131 and an external computer 136. Other components are also possible.

The external electrocardiograph machine 133, or similar device, can capture an electrocardiogram of the patient 10 at different points of the pacing therapy, as described supra, which can be used to identify physiology indicative of a presence of Brugada syndrome in the patient. The external electrocardiograph machine 133 can be a conventional electrocardiograph machine that uses a set of twelve precordial leads 134 (shown as a single across-the-chest "strap" for the sake of simplicity) to record an electrocardiogram. Further, the external electrograph machine 133 can be used to determine the level of cardiac electrical asynchrony that occurs when the therapeutic electrical stimulation is applied via the pacing electrode 23 to the potential pacing sites. As described in the U.S. Pat. No. 9,392,949, issued on Jul. 19, 2016, to Ortega et al, the disclosure of which is incorporated by reference, at least two of the precordial leads can be used to collect the signals used to quantify the asynchrony. In a further embodiment, the external electrocardiograph machine 133 relies on the implantable CRM device 19 to temporally capture cardiac cycle physiology, which is then interpreted by either the external electrocardiograph machine 133 or an external computer 136, as described infra, into an electrocardiogram or similar form of temporal mapping of the cardiac cycle physiology. Likewise, the signals used to evaluate the cardiac electrical asynchrony of the potential pacing sites can be obtained using the sensing electrodes 24, 26 of the CRM device 19. The signals, obtained using the external electrograph machine 133 or the CRM device, can be processed by the external electrograph machine 133, the external computer 136, or another processing device to quantify the asynchrony level associated with application of pacing to each of the potential pacing sites tested.

The conventional external programmer 131, or similar device, can remotely communicate with the implantable CRM device 19 using an inductive (or wireless) communications channel to enable remote parametric programming of and stored physiologic data offload from the device. The programmer 131 includes a physically-connected programmer wand 132, which is placed by health care personnel over the patient's pectoral region above the implantable CRM device 19 to initiate and carry out programmer-to-CRM device communications.

The external computer 136, or similar device, can be wirelessly (or inductively) interfaced to the implantable CRM device 12. The external computer 136 receives cardiac cycle physiology, as recorded by the implantable CRM device 12 via the wireless communications channel. Alternatively, cardiac cycle physiology or, equivalently, electrocardiograms, can be retrieved by the external computer 136 from the external electrocardiograph machine 133, or other source. The external computer 136 algorithmically identifies physiology indicative of a presence of Brugada syndrome in the patient 10. In addition, the external computer 136 can create an individualized algorithm for each patient 10 that maps the changes in the intracardiac electrocardiographic patterns that are detected with the implanted sensing electrodes 24, 26 to the presence or absence of the Brugada syndrome electrocardiographic pattern as registered in the cardiac cycle physiology or electrocardiograms.

Finally, the system 130 can include a centralized server 137 coupled to a database 138 within which patient data, such as the electrocardiograms and algorithms, are stored. The external electrocardiograph machine 133, external programmer 131, and the external computer 136 can interface with the centralized server 137 through a network 135, such as a publicly available wide area network, including the Internet. Other forms of remote server interfacing are possible.

In a yet further embodiment, the system 130 can be adapted for use in EPS, whereby a transiently-introduced electrophysiology catheter 190, shown with reference to FIG. 20, serves the functions of the implantable CRM device 19, which can either be temporarily rendered inoperable or be absent from the patient 10 altogether.

Figure 16:
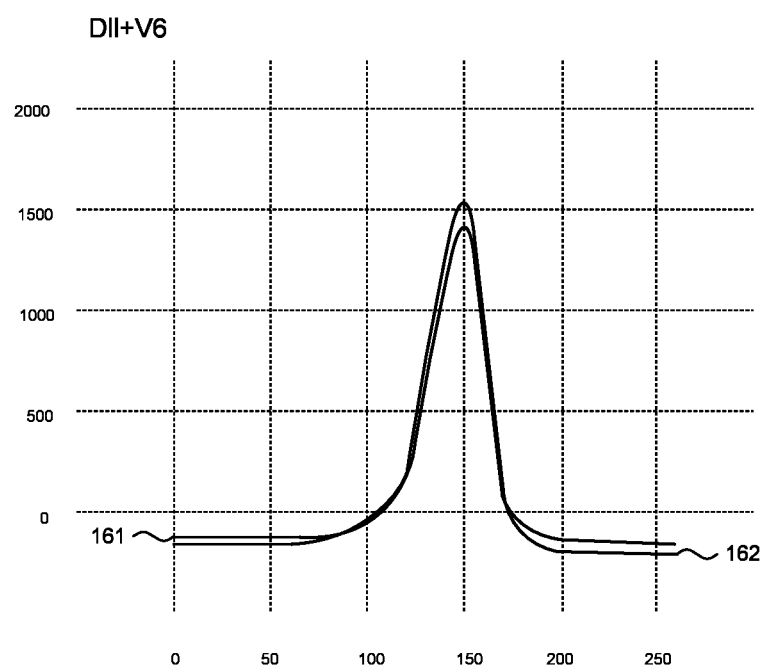
FIG. 16 shows surface ECG curves representing both left ventricle and right ventricle of a patient superimposed in their final portion, with the left ventricle and the right ventricle exhibiting a high degree of synchrony.

Identifying pacing sites associated with a minimal level of cardiac asynchrony allows to treat Brugada syndrome with conventional waveform pacing. FIG. 15 is a flow diagram showing a routine 150 for selecting a site for delivering therapeutic stimulation by the pacing electrode in the region near the His bundle 16 or the para-Hisian region 17 for use in the methods of FIGS. 4 and 5 in accordance with one embodiment. While in the description below, the endocardial lead 21 is described as a screw-in lead, in a further embodiment, use of other kinds of leads 21 is possible. Initially, the endocardial screw-in lead 21 is inserted into the patient 10 (step 151). Right or left venous access can be used for the insertion. Cephalic, subclavian or axillary venous approach can be used through dissection or puncture for the insertion. If puncture is used, a peel-away sheath is placed over a short guidewire. The endocardial lead 21 is then advanced towards the peel-away sheath guided by fluoroscopy. The lead 21 is positioned in pulmonary artery. A curved stylet is advanced into the lead 21. Then the stylet is located and fixed in atrial floor. The lead 21 is removed slowly while the stylet remains fixed. At this time, right ventricular septal zone is mapped with an apparatus that determines a level of cardiac asynchrony associated with each of the pacing sites in the zone (step 152), such as the apparatus described in the U.S. Pat. No. 9,392,949, issued on Jul. 19, 2016, to Ortega et al, the disclosure of which is incorporated by reference. One of the septal sites is selected for further pacing based on the mapping (step 153), with the pacing site associated with a lowest level of asynchrony. In one embodiment, the site most closely associated with an asynchrony curve shown with reference to FIG. 16 is selected. FIG. 16 shows surface ECG curves representing both right ventricle 161 and left ventricle 162 of a patient superimposed in their final portion, with the left ventricle and the right ventricle exhibiting a high degree of synchrony. In a further embodiment, other expressions of asynchrony, such as asynchrony indices, can be used to select the pacing site.

Returning to FIG. 15, once the pacing site is selected, the screw of the lead 21 is released and the stylet is removed, (step 154). Sensing and threshold measurements are performed (step 155). Defibrillation threshold is tested to ensure that defibrillation that can be delivered is capable of terminating arrhythmia (156). If the sensing and threshold measurements and the tested defibrillation threshold in steps 155 and 156 are within normal ranges (step 157), the lead 21 is then fixed in the selected site as the final position (158), allowing pacing described above beginning with reference to steps 62 and 82 and ending the routine 150. If the sensing and threshold measurements and the tested defibrillation threshold in steps 155 and 156 are not within a normal range (step 157), a different site is selected based on the asynchrony data obtained in step 153, the lead 21 is repositioned in a the different site (step 160), and the routine 150 returns to step 155.

While the invention has been particularly shown and described as referenced to the embodiments thereof, those skilled in the art will understand that the foregoing and other changes in form and detail may be made therein without departing from the spirit and scope.

What is claimed is:

1. A system for Brugada syndrome detection and treatment via electrical stimulation comprising:

a cardiac pacing device comprising a pulse generator and at least one pacing electrode that is electrically coupled to the pulse generator via an endocardial lead, the at least one pacing electrode configured to be positioned in one of a plurality of potential pacing sites that is selected based on a level of cardiac electrical asynchrony associated with that potential pacing site and based on a defibrillation shock being capable of being delivered to the site, the selected potential pacing site located in one of a region near the His bundle and a para-Hisian region of a patient's heart, the pulse generator configured to deliver through the at least one pacing electrode therapeutic electrical stimulation substantially coincidentally to propagation of an activation wave front proceeding from the atrioventricular node of the patient's heart when the at least one pacing electrode is positioned at the selected potential pacing site, the cardiac pacing device further comprising a cardioverter defibrillator coupled to the endocardial lead; and a diagnostic module operatively coupled to the pulse generator and configured to sense via at least one sensing electrode physiology indicative of a presence of Brugada syndrome in the patient, to detect the presence of the Brugada syndrome, the diagnostic module further configured to control the pulse generator in delivering the electrical therapeutic electrical stimulation at the selected potential pacing site in response to the presence of Brugada syndrome, and to control the cardioverter defibrillator to deliver via the endocardial lead the defibrillator shock to the patient.

* * * * *